United States Patent [19]
Singh et al.

[11] Patent Number: 6,133,485
[45] Date of Patent: Oct. 17, 2000

[54] ASYMMETRIC SYNTHESIS OF 2-(2,4-DIFLUOROPHENYL)-1-HETEROCYCL-1-YL BUTAN-2,3-DIOLS

[75] Inventors: Inder Pal Singh; Inderjit Sidhu; Bhupinder Palak, all of Edmonton; Ronald G. Micetich, Sherwood Park, all of Canada

[73] Assignees: Synphar Laboratories, Inc., Alberta, Canada; Taiho Pharmaceuticals Co., Ltd., Tokyo, Japan

[21] Appl. No.: 09/060,138

[22] Filed: Apr. 15, 1998

[51] Int. Cl.[7] .................................................. C07C 27/10
[52] U.S. Cl. ............................................................ 568/700
[58] Field of Search ............................................... 568/700

[56] References Cited

U.S. PATENT DOCUMENTS

| | | | |
|---|---|---|---|
| 5,126,494 | 6/1992 | Gilheany et al. | 568/700 |
| 5,204,333 | 4/1993 | Giese et al. | 568/700 |
| 5,227,543 | 7/1993 | Sharpless et al. | 568/700 |
| 5,260,461 | 11/1993 | Hartung et al. | 568/700 |
| 5,278,070 | 1/1994 | Shum | 568/700 |
| 5,371,100 | 12/1994 | Itoh | 568/700 |
| 5,371,101 | 12/1994 | Itoh et al. | 568/700 |
| 5,445,763 | 8/1995 | Schlosser et al. | 568/700 |
| 5,516,929 | 5/1996 | Sharpless et al. | 568/700 |
| 5,629,428 | 5/1997 | Schlosser et al. | 568/700 |
| 5,645,652 | 7/1997 | Itoh et al. | 568/700 |

FOREIGN PATENT DOCUMENTS

| | | | |
|---|---|---|---|
| 0 332 387 | 3/1989 | European Pat. Off. . | |
| 0 332 387 | 9/1989 | European Pat. Off. | 568/700 |
| 0 728 752 | 9/1990 | European Pat. Off. . | |
| 0 522 655 | 7/1992 | European Pat. Off. . | |
| 0 612 734 | 8/1994 | European Pat. Off. | 568/700 |
| 3-128338 | 5/1991 | Japan . | |
| WO 91/03451 | 3/1991 | WIPO . | |
| WO 93/13093 | 7/1993 | WIPO . | |
| WO 93/20068 | 10/1993 | WIPO . | |
| WO 93/20069 | 10/1993 | WIPO . | |
| WO 95/22973 | 8/1995 | WIPO . | |
| WO 96/25410 | 8/1996 | WIPO . | |

OTHER PUBLICATIONS

Konosu, et al., Chem Pharm. Bull. 39(9) 2241–2246 (1991), "Triazole Antifungals. III. Stereocontrolled Synthesis of an Optically Active Triazolymethyloxirane Precursor to Antifungal Oxazolidine Derivatives".

Tasaka, et al., Chem. Pharm. Bull. 41(6) 1035–1042 (1993), "Optically Active Antifungal Azoles. I. Synthesis and Antifungal Activity of (2R,3R)–2–(2, 4–Difluorophenyl)–3–mercapto–1–(1H–1,2, 4–triazol–1–yl)–2–butanol and Its Stereoisomers".

Tasaka, et al., Chem. Pharm. Bull. 45(2) 321–326 (1997), "Optically Active Antifungal Azoles. VII. Synthesis and Antigungal Activity of Stereoisomers of 2–[1R,2R)–2–(2, 4–Difluorophenyl)–2–hydroxy–1–methyl–3–(1H–1, 2–4–triazol–1–yl)propyl]–4–[4–(2,2,3,3–tetrafluoropropoxy)phenyl]–3(2H,4H)–1,2,4–triazolone (TAK–187)".

Kitazaki, et al., Chem. Pharm. Bull. 44(2) 314–327 (1996), "Optically Active Antifungal Azoles. VI. Synthesis and Antifungal Activity of N–[(1R,2R)–2–(2, 4–Difluorophenyl)–2–hydroxy–1–methyl–3–(1H–1,2, 4–triazol–1–yl)proopyl]–N'–(4–substituted phenyl)–3(2H, 4H)–1,2,4–triazolones and 5(1H,4H)–tetrazolones".

Girijavallabhan, et al., Bioorganic & Medicinal Chemistry Letters, vol. 1, No. 7, pp. 349–352 (1991), Synthesis of the Antifungal Agent SCH 42427[1](SM 9164).

*Primary Examiner*—Louise N. Leary
*Attorney, Agent, or Firm*—Arent Fox Kintner Plotkin & Kahn

[57] ABSTRACT

The asymmetric production of pure diastereomeric (2R,3R), (2R,3S), (2S,3R) and (2S,3S)-2-aryl-1-substituted butan-2, 3-diols from the derivatives of lactic acid.

34 Claims, No Drawings

ASYMMETRIC SYNTHESIS OF 2-(2,4-DIFLUOROPHENYL)-1-HETEROCYCL-1-YL BUTAN-2,3-DIOLS

FIELD OF INVENTION

The present invention is concerned with the asymmetric production of pure diastereomeric. (2R,3R), (2R,3S), (2S,3R) and (2S,3S)-2-(2,4-difluorophenyl)-1-(1,2,4-triazol-1-yl)butan-2,3-diols from the derivatives of lactic acid.

Asymmetric diols of general formula 9

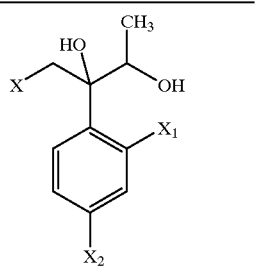

are important intermediates used in the preparation of various azole derivatives useful as antifungal agents, such as SM-8668 I, (Genaconazole)[1], II[2], III[3], IV[4].

I

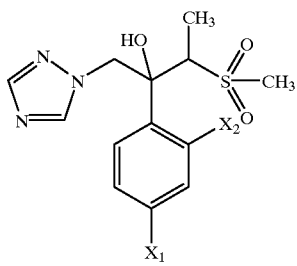

II

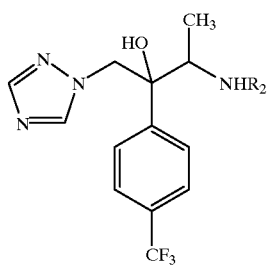

III

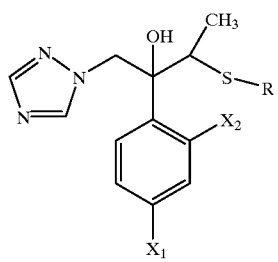

IV

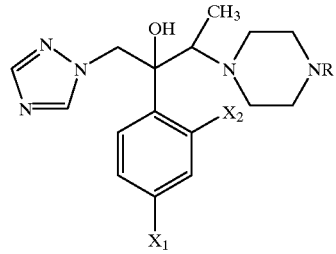

There are several synthetic procedures[2,3,8] developed and reported in the literature for the preparation of racemic mixtures of the above diols. Another published method[5] is related to the asymmetric (2R,3R) -3-(2,4-difluorophenyl)-3,4-epoxy-2-butanol, at intermediate used for the preparation of the title compounds and produces the (2R,3R) diastereomer which is contaminated with appreciable amounts of the (2R,3S) diastereomer. The scheme route described in the above publication is summarized below in Scheme-A.

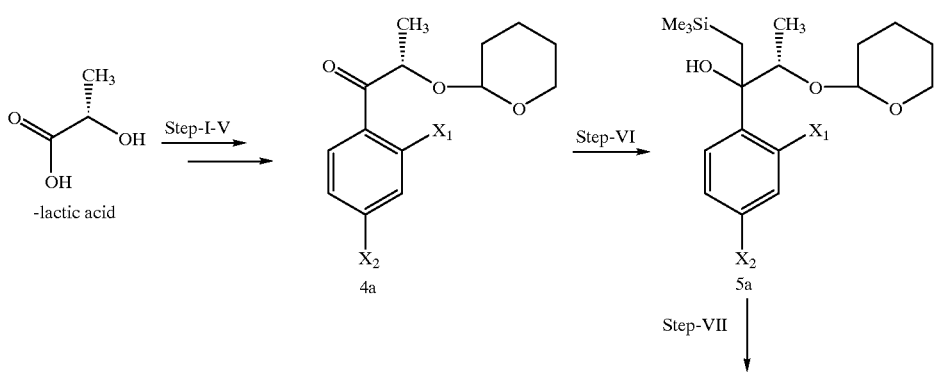

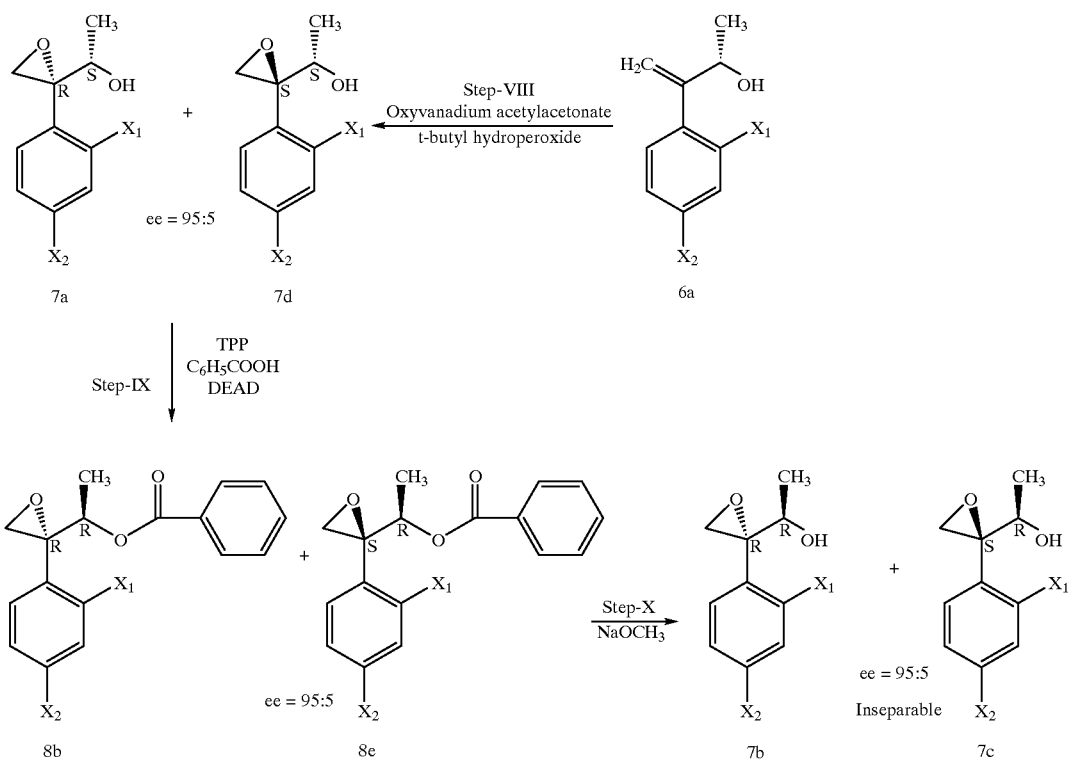

The above process has the following disadvantages:

First, it takes several steps to reach the intermediate 4a from the starting material, S-lactic acid.

Second, the conversion of the keto group of 4a into the methylene group to obtain the intermediate 6a requires chemicals like trimethyl silylmagnesium chloride, which are not commercially available in bulk and should be prepared on site. This contributes to additional time, labor and expenses.

Third, step-VI utilizes benzene to recover the intermediate 5a. Benzene is a known hazardous solvent which does not metabolize in the human body, therefore, raise serious health concerns.

Fourth, the allylic alcohol on epoxidation (step-VIII) gives a mixture of the (2S,3R) and (2S,3S) -3-(2,4-difluorophenyl)-3,4—2-butanols (7a and 7d). The crude has to be purified for the next step. The required diastereomer (2S,3R) -3-(2,4-difluorophenyl)-3,4-epoxy-2-butanol could not be obtained in a pure chiral form as the undesired diastereomer is inseparable from the product mixture.

Fifth, the mixture of 7a and 7d are then converted into their corresponding benzoates (8a and 8c, step-IX), which has to be separated and purified. The purification used does not remove the undesired diastereomer completely from the mixture. Isolation and purification add to the cost of labor, solvents and time without really providing pure diastereomer. The yields reported therein also could not be reproduced in our hands.

Sixth, the benzoates are solvolized (step-X) and the final product has to be purified by silica gel chromatography. After purification the purified product was found to be still contaminated with the undesired (2R,3S)-3-(2,4-difluorophenyl)-3,4-epoxy-2-butanol diastereomer(7c).

On the basis of the above mentioned facts, it is clear that the described process is not a suitable process for the large scale production of the diastereomerically pure (2R,3R) -3-(2,4-difluorophenyl)-3,4-epoxy-2-butanol product.(7b) The process requires column chromatography at each step which contributes to increased labor, chemicals, extraction and purification costs. Even after purification the required product (2R,3R)-3-(2,4-difluorophenyl)-3,4-epoxy-2-butanol(7b) is only 95% pure and the rest is its unrequired diastereomer (7c).

The present invention, therefore, concerns a more efficient new method for enantioselective synthesis of the pure desired diastereomers 7a, 7b, 7c, 7d, 9a, 9b, 9c and 9d starting from the commercially available derivatives of lactic acid.

SUMMARY OF THE INVENTION

This invention deals with new improved methods for the stereo selective synthesis of the optically active diastereomeric (2S,3R), (2R,3R), (2R,3S) and, (2S,3S) -3-(2,4-difluorophenyl)-3,4-epoxy-2-butanols(7a -7d) in >99% enantiomeric purity and the (2R,3S), (2R,3R), (2S,3R) and (2S,3S), 2-(2,4-difluorophenyl)-1-(1,2,4-triazol-1-yl)-butan-2,3-diols of the general formula 9a–d in almost 100% enantiomeric purity.

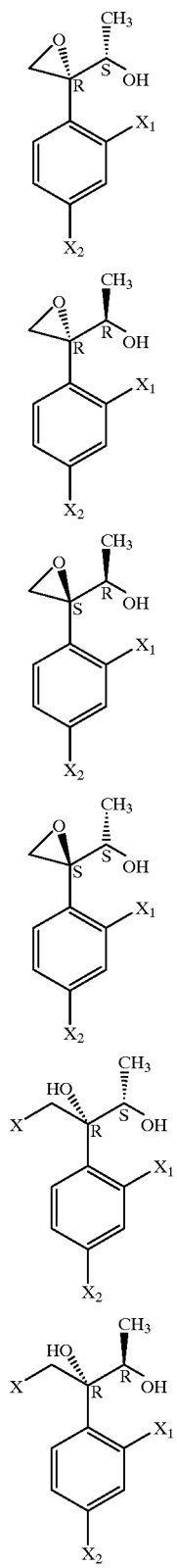

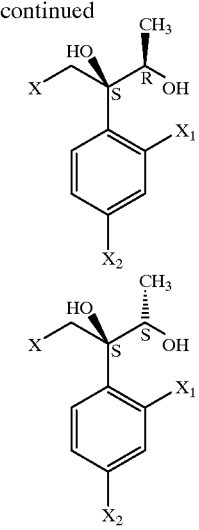

The procedures for the diastereoselective synthesis of 7a–7d and 9a–9d are reported in the Schemes-B, C, D and E.

The invention provides the production of (2S,3R)-3-(2,4-difluorophenyl)-3,4-epoxy-2-butanol (7a) and (2R,3S)-3-(2,4-difluorophenyl)-3,4-epoxy-2-butanol (7c) from the intermediates 4a and 4b respectively (Schemes B and D) in nearly 100% diastereomeric yield. From the NMR, the products (7a and 7c) seem to be free of undesired diastereomer.

This invention provides methods for the absolute inversion of configuration at the chiral carbon in high yield.

It utilizes p-nitrobenzoic acid instead of benzoic acid in step VII (Scheme-C and E) which provides better purity and yield of the final compounds (2R,3R)-and (2S,3S)-2-(2,4-difluorophenyl)-1-(1,2,4-triazol-1-yl) butan-2,3-diols (9b and 9d respectively).

The present invention provides faster and economical methods for manufacturing the diastereomerically pure compounds 9a–9d as free bases or as their hydrochlorides, free from contaminant without a need for expensive purification by chromatography.

The reaction steps-VII, VIII and IX (Scheme-C and E) can be carried out in one pot to produce the final diols (2R,3R)-and (2S,3S)-2-(2,4-difluorophenyl)-1-(1,2,4-triazol-1-yl) butan-2,3-diols (9b and 9d) in pure crystalline form in one pot from the intermediate 7a and 7c respectively without going through time consuming isolation and purification of the involved intermediates.

It utilizes p-nitrobenzoic acid to produce the final compounds (2R,3R)-and (2S,3S)-2-(2,4-difluorophenyl)-1-(1,2,4-triazol-1-yl) butan-2,3-diols (9b and 9d) in one pot directly from intermediates (7a and 7c respectively) which leads to higher quality products without going through costly isolation and purification steps.

DESCRIPTION OF THE PREFERRED EMBODIMENTS

The present invention describes new methods for the commercial production of the following diastereomerically pure compounds:

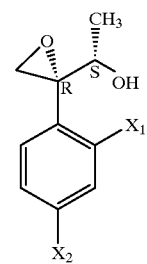

7a

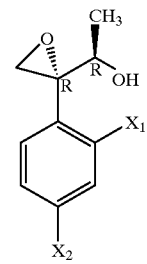

7b

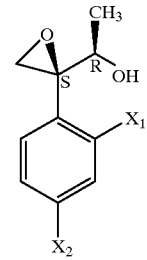

7c

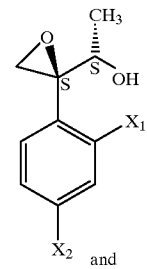

7d

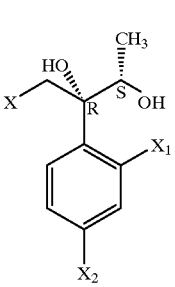

and

9a

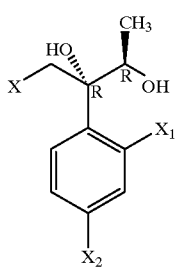

9b

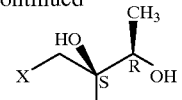

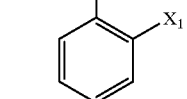

-continued

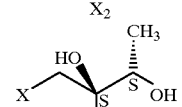

9c

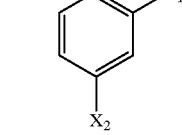

9d wherein $X_1$ and $X_2$ are the same or different and represent a hydrogen or any of chloro, bromo or fluoro substituent or a lower alkyl or alkoxy which may be further substituted with halogens like chloro, bromo or fluoro; wherein X is selected from the group consisting of:

(1) N—$(R_1)(R_2)$, wherein $R_1$ and $R_2$ are each independently hydrogen or phenyl, wherein the phenyl is unsubstituted or substituted with chlorine, bromine, fluorine, $NO_2$, $C_1$–$C_6$ alkyl group and $C_1$ to $C_6$ alkoxy group, wherein the $C_1$–$C_6$ alkyl and $C_1$–$C_6$ alkoxy groups are unsubstituted or have a substituent selected from the group consisting of chlorine, bromine, fluorine and phenyl, wherein the phenyl is unsubstituted with chlorine, bromine, fluorine, $NO_2$, $C_1$–$C_6$ alkyl group and $C_1$–$C_6$ alkoxy group;

(2) S—$R_1$, wherein $R_1$ is as defined above;

(3) O—$R_1$, wherein $R_1$ is as defined above;

(4) S(O)—$R_1$, wherein $R_1$ is as defined above;

(5) $S(O)_2$—$R_1$, wherein $R_1$ is as defined above; and (6) a five, ;ix or seven membered heterocycle with 1–3 heteroatoms each independently selected from the group consisting of N, S, S(O), $S(O)_2$ and O, wherein the heterocycle is attached to the remainder of the compound via a heteroatom or a carbon.

Examples of the $C_1$–$C_6$ alkyl group includes linear or branched alkyl groups such as methyl, ethyl, n-propyl, isopropyl, n-butyl, isobutyl, sec-butyl, tert-butyl, pentyl and hexyl.

Exemplary ($C_1$–$C_6$ alkoxy group includes liner or branched alkoxy groups such as methoxy, ethoxy, n-propoxy, isopropoxy, n-butoxy, isobutoxy, sec-butoxy, tert-butoxy, n-pentyloxy, isopentyloxy and n-hexyloxy.

Scheme-B, C, D and E describe the synthesis of (2R,3R), (2R,3S), (2S,3R) and (2S,3S)-2-(2,4-difluorophenyl)-1-(1,2,4-triazol-1-yl) butan-2,3-diols in a stepwise manner starting from commercially available optically active methyllactates. Methodology to obtain each of the above compounds is given in the General Experimental section. The chiral intermediates 4a and 4b are prepared by following the literature methods[3]. The intermediate 4a and 4b are then converted to the exomethylene intermediate 5a and 5b respectively by reacting them with methyl triphenyl phosphonium bromide in the presence of sodium bis trimethylsilyl amide or lithium bis trimethylsilyl amide in tetrahydrofuran. The compounds 5a and 5b, after deprotection, provide the substituted allyl-alcohols of the general formula 6a and 6b respectively which are then reacted with tert-butyl hydroperoxide in the presence of titanium isopropoxide and chiral tartrate following the "Sharpless" stereo selective epoxidation method[6], in an aprotic solvent, such as dichloromethane at a temperature of −15° C. to 25° C. to generate an asymmetric center with high diastereomeric yields.

The compounds 7a and 7c thus produced are converted into the corresponding esters 8a, 8b, 8c and 8d with quantitative inversion of configuration at the C2 carbon by reacting with an appropriate carboxylic acid preferably p-nitrobenzoic acid, in the presence of triphenylphosphine and diethyl azodicarboxylate. The solvolysis of these esters in the presence of sodium methoxide yields compounds 7b and 7d respectively in high diastereomeric access and yield.

In step VII (Scheme-C and E) the use of benzoic acid results in lower yields of the corresponding benzoates which inturn on solvolysis gives poor yields of the (2R,3R)-3-(2,4-difluorophenyl-3,4-)-2-butanols(7b) and (2S,3S)-3-(2,4-difluorophenyl)-3,4-epoxy-2-butanols(7d) The use of p-nitrobenzoic acid instead of benzoic acid reduces the overall reaction time, improves the overall yield and the quality of the products (8a and 8c). The diols (2b and 9d), which are obtained by the reaction of 1,2,4-triazole on 7b and 7d respectively, are isolated from the reaction mixture as their hydrochlorides or free bases. The recovered products are diastereomerically pure and free from undesired diastereomers.

Reaction of the 1,2,4-triazole on compounds 7a–d in N,N-dimethylformamide or acetonitrile in the presence of a base, such as potassium carbonate, cesium carbonate, NaH or sodium methoxide at 0–80° C. followed by crystallization produces the corresponding enantiomerically pure 2-(2,4-difluorophenyl)-1-(1,2,4-triazol-1-yl) butan-2,3-diols of the general formula 9a to 9d (Schemes C and E, steps VII–IX and X).

All the reactions described in Schemes B to E are preferably done from the crude intermediates to prepare enantiomerically pure 2-(2,4-difluorophenyl)-1-(1,2,4-triazol-1-yl) butan-2,3-diols of the general formula 9a–d, starting from the respective methyl lactate. The final products 9a–9d can be isolated by crystallization from their crude reaction products.

Alternatively and preferably the reaction steps (VII, VIII and IX; Scheme-C and E ) can be conducted sequentially essentially in one pot to get the diastereomerically pure title compounds 9b and 9d as their hydrochlorides without work-up, isolation or purification of any of the intermediates 8a- to 8d, 7b or 7d. The diastereomers 9b and 9d are obtained free from undesired diastereomers.

The use of p-nitrobenzoic acid instead of benzoic acid in a one pot process also results in higher yields of the isolated pure corresponding products, the 2-(2,4-difluorophenyl)-1-(1,2,4-triazol-1-yl) butan-2,3-diols (9b and 9d).

In addition to the shown protecting group tetrahydropyrane for substituent R, other appropriate protecting group also may include trimethylsilyl, t-butyldimethyl silyl, benzyl, trityl, methoxymethyl, methoxyethoxymethyl, acetyl and benzoyl, etc. A worker of skill in the art can choose a suitable protecting group from literature in the art, such as Greene et al (1981), "Protective Groups in Organic Synthesis", the entire contents of which are hereby incorporated by reference.

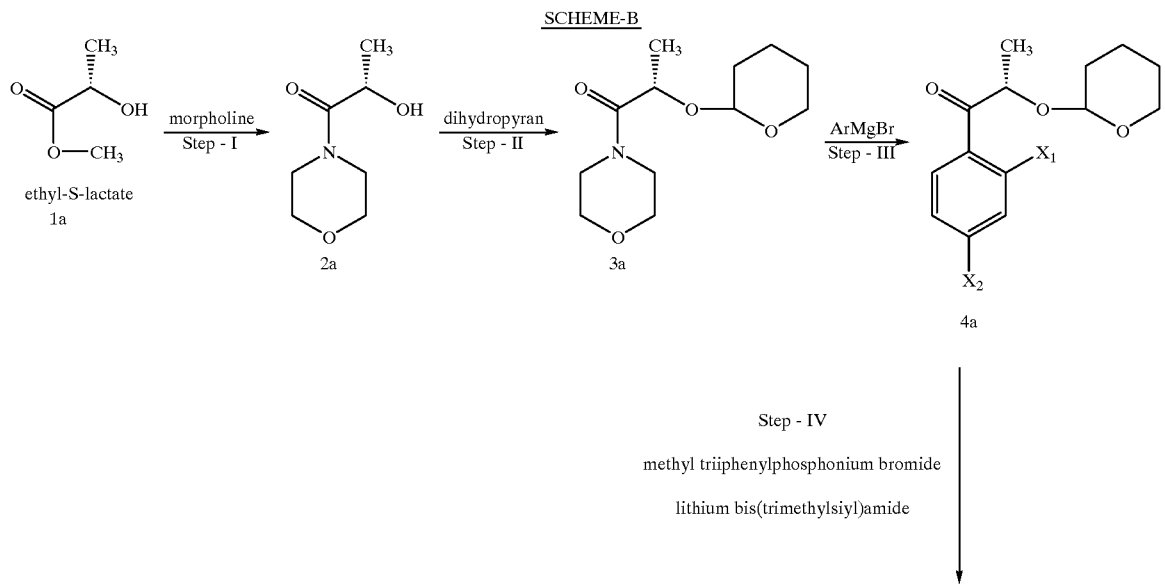

SCHEME-B

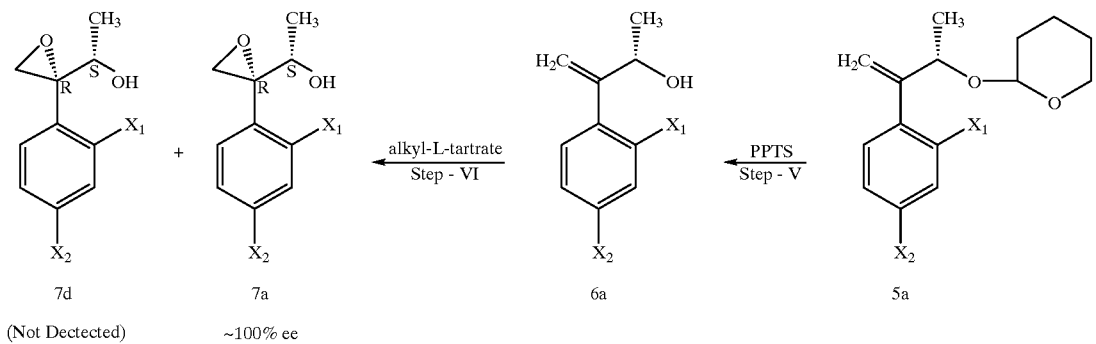
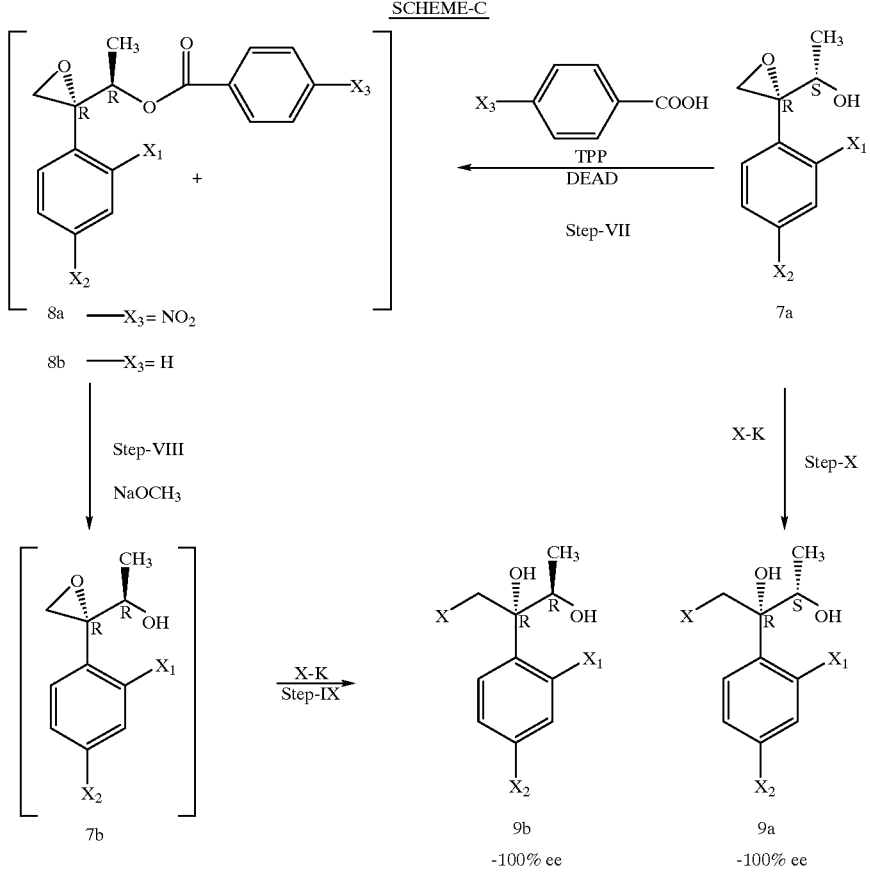
SCHEME-C

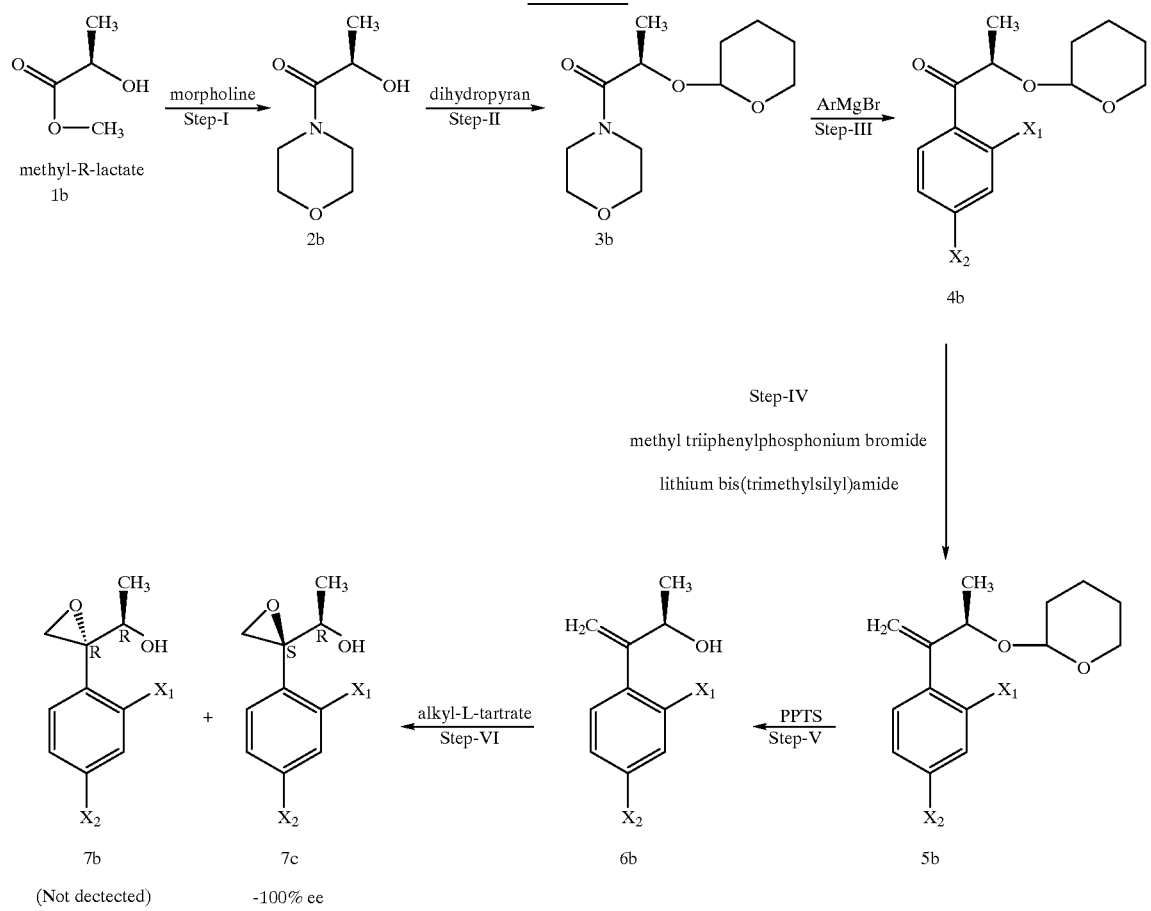
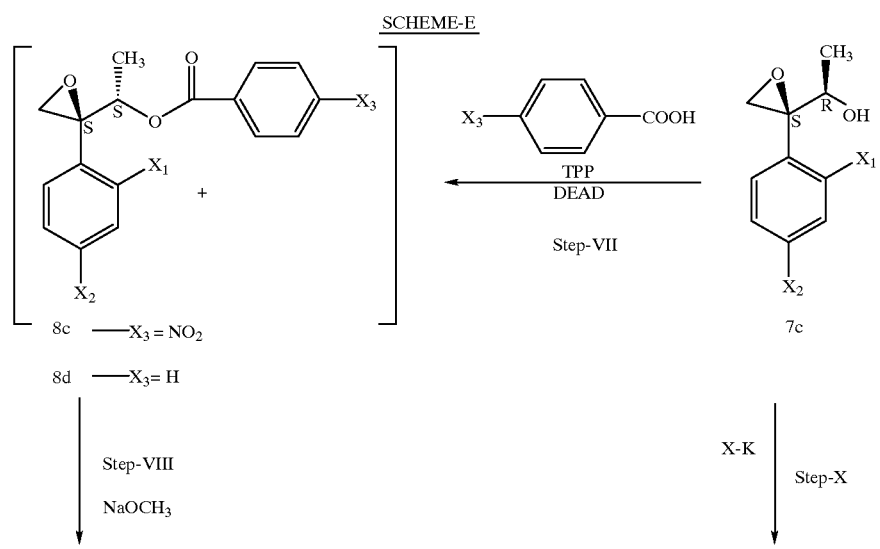

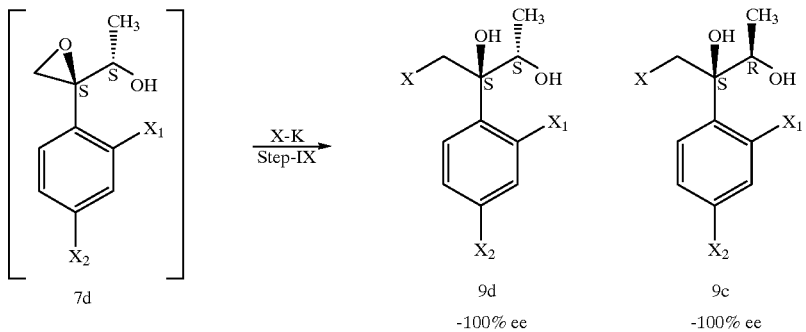

EXAMPLES

Example 1
(3S)-2-(2,4-Difluorphenyl)-3-(3,4,5,6-tetrahydro-2H-pyran-2-yloxy)-1-butene [5a]

A mechanically stirred mixture of methyl triphenylphosphonium bromide (169.2 g, 0.474 moles) in 350 ml of dry tetrahydrofuran was cooled to 8° C. A solution of lithium bis (trimethylsilyl) amide (84.8 g, 0.507 moles) in 500 ml tetrahydrofuran was added to the above mixture at a rate so that the temperature of the mixture remained at 23° C. After stirring for 1 hour at room temperature the contents were cooled to 31 70° C. and stirred for ½ hour. Then a solution of compound 4a, (2S)-2',4'-Difluoro-2-(3,4,5,6-tetrahydro-2H-pyran-2-yloxy)propiophenone, (100 g, 0.370 moles) in 250 ml of tetrahydrofuran was added slowly to maintain the temperature of the mixture below −70° C. The resulting mixture was stirred at 7° C. for 17 hours. Added 65 ml of ethyl acetate to the above mixture followed by the addition of 3.9 L of hexane and allowed to stand for 15 minutes. The solid was removed by suction-filtration and washed thoroughly with 650 ml of hexane. The filtrate was washed with 1:1 mixture of methanol: water (2×1300 ml) and brine (1300 ml) then dried over $MgSO_4$. The solvent was evaporated to give the title compound 5a as an oil (91.5 g, 92%).

$^1$H-NMR (CDCl$_3$) δ: 1.20(d, 3H, J=6.54 —CH$_3$), 1.48–1.80(m, 6H), 3.36–3.53(m, 1H), 3.63–3.93(m, 1H), 4.54–4.64(q, 1H, J=6.5 Hz, —CH), 4.69–4.79(m, 1H), 5.15 (m, 1H), 5.50(d, 1H), 6.69–6.82(m, 2H, Ar—H), 7.09–7.28 (m, 1H, Ar—H) ppm.

Example 2
(2S)-3-(2,4-Difluorophenyl)-3-buten-2-ol [6a]

A mixture of compound 5a, (3S)-2-(2,4-Difluorophenyl)-3-(3,4,5,6-tetrahydro-2H-pyran-2-yloxy)-1-butene, (81 g, 0.302 mole) and pyridinium-p-toluenesulfonate (32.7 g, 0.130 mole) in 1200 ml of ethanol was heated at 60° C. for 9 hours. The reaction mixture was concentrated in vacuo and co-evaporated with toluene. Toluene was then added to the residue and the resulting solid was removed by filtration. The filtrate was evaporated under reduced pressure and the residue was chromatographed on silica gel. Elution with 10% ethyl acetate in hexane gave the title compound 6a as light yellow oil (44.96 g, 81%)

$^1$H-NMR (CDCl$_3$) δ: 1.26(d, 3H, J=6.43, —CH$_3$), 2.25(b, s, 1H, —OH), 4.69(m, 1H, CH), 5.17(s, 1H, =CH$_2$), 5.55(s, 1H, =CH$_2$), 6.75–6.90(m, 2H, Ar—H), 7.17–7.29(m, 1H, Ar—H) ppm.

Example 3
(2S, 3R)-3-(2,4-Difluorophenyl)-3,4-epoxy-2-butanol [7a]

To a solution of diethyl L(+)-tartrate (2.43 g, 0.0118 mole) in 470 ml of dry CH$_2$Cl$_2$ were added activated 3A° molecular sieve powder (6 g) and cooled the mixture to −5° C. Added a solution of titanium (IV) isopropoxide (7.2 g, 0.0253 mole) in 38 ml of CH$_2$Cl$_2$ followed by t-butyl hydroperoxide (11.2 g, 0.124 mole) in 75 ml of CH$_2$Cl$_2$ and continue to stir at −5° C. for 25 minutes. To this mixture, a solution of compound 6a, (2S)-3-(2,4-Difluorophenyl)-3-buten-2-ol, (7.5 g, 0.041 mole) in 38 ml of CH$_2$Cl$_2$ was added and stirred for 12 hours at 5° C. Cooled the reaction mixture to −40° C., added 20 ml of 30% aq. NaOH solution saturated with NaCl and the mixture was allowed to warm to 10° C. 20 g of MgSO$_4$, 6 g of celite was added to the mixture and continued to stir at 10° C. for 30 minutes. The mixture was suction-filtered over celite. To the filtrate 280 ml of toluene, 225 ml of ether were added and insoluble material removed by filtration. The filtrate was evaporated in vacuo, the residue was dissolved in 200 ml of ether and suction filtered to remove the insoluble material. The filtrate was passed through a bed of silica gel and washed the pad of silica gel with 20 ml of ether. The filtrate was concentrated under reduced pressure to give yellow oil, which was chromatographed on silica gel. Elution with CHCl$_3$ gave title compound 7a as an oil (3.5 g, 43%).

$^1$H-NMR(CDCl$_3$) δ: 1.16(d, 3H, J=6.22, —CH$_3$), 2.69(b, 1H, —OH), 2.88–2.96(m, 1H, epoxide), 3.27–3.30(m, 1H, epoxide), 4.10(m, 1H, —CH), 6.78–6.94(m, 2H, Ar—H), 7.32–7.44(m, 1H, Ar—H) ppm.

Example 4
(2R,3S)-2-(2,4-Difluorophenyl)-1-(1H-1,2,4-triazol-1-yl)-2,3-butanediol [9a]

To an ice cooled suspension of dry NaH (0.216 g, 0.009 mole) in N,N-dimethylformamide (10 ml), 1H-1,2,4-Triazole (0.691, 0.010 mole) was added in small portions under an atmosphere of nitrogen. The mixture was slowly brought to room temperature and a solution of compound 7a, (2S,3R)-3-(2,4-Difluorophenyl)-3,4-epoxy-2-butanol (1.0 g, 0.005 mole) in N,N-dimethylformamide (2 ml) was added. The resulting mixture was heated at 80° C. for 2 hours. The solvent was removed under reduced pressure and 50 g of crushed ice was added to the residue. The so formed mixture was extracted with ethyl acetate (100 ml, 2×50 ml). The combined organic layers were washed with water (20 ml) brine (50 ml) and dried over MgSO$_4$. The solvent was removed in vacuo and the residue was chromatographed on silica gel. Elution with methanol in chloroform (0% −3%) gave the title compound 9a as an amorphous solid (0.5 g, 37%).

$^1$H-NMR (CDCl$_3$) δ: 1.25(d, 3H, J=6.44, —CH$_3$), 2.89(b, s, 1H, —OH), 4.01(m, 1H, —CH), 4.51–4.58(m, 1H), 4.99–5.05(m, 2H), 6.65–6.85(m, 2H, Ar—H), 7.47–7.59(m, 1H, Ar—H), 7.73(s, 1H, Het-H), 8.02(s, 1H, Het-H) ppm.

Example 5
(2R, 3R)-3-(2,4-difluorophenyl)-3,4-epoxybutyl 4'-nitrobenzoate [8a]

A solution of compound 7a (1.4 g, 0.007 mole), triphenylphosphine (2.24 g, 0.0084 mole), and p-nitrobenzoic acid (1.4 g, 0.0084 mole) in 30 ml of dry tetrahydrofuran was cooled to 0° C. Into this clear solution, diethyl azodicarboxylate (1.32 ml, 0.0084 mole) was dropped slowly and the resulting mixture was stirred for 1 hour at 0° C. The solvent was evaporated under reduced pressure and the residue was partitioned between ethylacetate (75 ml) and water (15 ml). The organic phase was washed with water, brine and dried over sodium sulfate. After filtration, the solvent was evaporated and the residue was chromatographed on silica gel column. Elution with 5% ethylacetate in hexane gave the (2R, 3R)-(2,4-difluorophenyl)-3,4-epoxybutyl 4'-nitro-benzoate [8a] as an oil (1.52 g, 62% yield).

$^1$H-NMR (CDCl$_3$) δ: 1.40(d, 3H, J=6.90 Hz, —CH$_3$), 2.99(d, 1H, J=4.89 Hz, epoxide), 3.29(d, 1H, J=4.89 Hz, epoxide) 5.40(q, 1H, —CH), 6.90–7.00(m, 2H, Ar—H), 7.42–7.55(m, 1H, Ar—H), 8.16–8.34(m, 4H, Ar—H) ppm.

Example 6
(2R,3R)-3-(2,4-difluorophenyl)-3,4-epoxybutyl benzoate [8b]

To an ice cooled solution of compound 7a (2.0 g, 10 mmole) in 20 ml of tetrahydrofuran, triphenylphosphine (3.02 g, 11.5 mmole), benzoic acid (1.40 g, 11.5 mmole), diethyl azodicarboxylate (2.0 g, 11.5 mmole) were added and stirred for 17 hours under N$_2$ at room temperature. The reaction mixture was diluted with ethyl acetate (70 ml) and washed with water (40 ml). The aqueous phase was extracted with ethyl acetate (2×20 ml). The combined organic layers were washed with water (20 ml), brine and dried over MgSO$_4$. The solvent was evaporated and the oily residue was chromatographed on silica gel. Elution with 4% ethyl acetate in hexane gave the title compound 8b as an oil (1.22 g, 40%).

$^1$H-NMR (CDCl$_3$) δ: 1.38(d, 3H, J=6.64, —CH$_3$), 2.90(d, 1H, J=4.94 Hz, epoxide), 3.24(d, 1H, J=5.03 Hz, epoxide) 5.40(q, 1H, —CH), 6.79–6.98(m, 2H, Ar—H), 7.40–7.61(m, 4H, Ar—H), 799–8.04(m, 2H, Ar—H) ppm.

Example 7
(2R,3S)-3-(2,4-Difluorophenyl)-3,4-epoxy-2-butanol [7b]
Method A

Into an ice cooled solution of NaOCH$_3$ (217 mg, 4.02 mmole) in 20 ml of CH$_3$OH was dropped a solution of compound 8a, (2R,3R)-3-(2,4-difluorophenyl)-3,4-epoxybutyl 4'-nitrobenzoate (1.08 g, 3.09 mmole) in 5 ml of CH$_3$OH and the resulting mixture stirred for 1 hour at 0° C. The solvent was evaporated under reduced pressure and 10 g of crushed ice was added to the residue. The mixture was extracted with ethyl acetate (2×40 ml). The combined organic layers were washed with water (10 ml), brine and dried over MgSO$_4$. After filtration the solvent was evaporated and the residue was chromatographed on silica gel. Elution with CHCl$_3$ gave the title compound 7b as an oil (565 mg, 91%).

$^1$H-NMR (CDCl$_3$) δ: 1.17(d, 3H, J=6.64, —CH$_3$), 1.78(b, s, 1H, —OH), 2.80(d, 1H, J=5.22, epoxide), 3.30(d, 1H, J=5.17, epoxide), 4.06–4.13(m, 1H), 6.76–6.92(m, 2H, Ar—H), 7.36–7.47(m, 1H, Ar—H) ppm.

Method B

Into an ice cooled solution of NaOCH$_3$ (231 mg, 4.3 mmole) in 40 ml of CH$_3$OH was dropped a solution of compound 8a (1.0 g, 3.3 mmole) in 10 ml of CH$_3$OH and the resulting mixture stirred for 2 hours at room temperature. The solvent was evaporated under reduced pressure and 20 g of crushed ice was added to the residue. The solution was acidified with 1N HCl and extracted with ethyl acetate (2×50 ml). The combined organic layers were washed with saturated NaHCO$_3$ (2×20 ml), water, brine and dried over MgSO$_4$. The solvent was evaporated and the residue was chromatographed on silica gel. Elution with CHCl$_3$ gave the title compound 7b as oil (500 mg, 76%).

$^1$H-NMR (CDCl$_3$) δ: 1.17(d, 3H, J=6.64, —CH$_3$), 1.78(b, s, 1H, —OH), 2.80(d, 1H, J=5.22, epoxide), 3.30(d, 1H, J=5.17, epoxide), 4.06–4.13(m, 1H), 6.76–6.92(m, 2H, Ar—H), 7.36–7.47(m, 1H, Ar—H) ppm.

Example 8
(2R,3R)-2-(2,4-Difluorophenyl)-1-(1H-1,2,4-triazol-1-yl)-2,3-butanediol [9b]
Method A A solution of compound 7b (560 mg, 2.8 mmole) in 15 ml of dry acetonitrile were added potassium carbonate (1161 mg, 8.4 mmole) and 1,2,4-triazole (580 mg, 8.,4 mmole). The resulting mixture was refluxed for 4 hour under nitrogen. After cooling, the solid was removed by suction filtration and washed with small amounts of ethylacetate. The filtrate was concentrated under reduced pressure and the residue was dissolved in 30 ml of ethylacetate. The resulting solution was washed with water (2×5 ml), brine and the organic phase was dried over sodium sulfate. The contents were suction filtered and the filtrate was diluted with 30 ml of diethyl ether. The solution was cooled and a steady stream of anhydrous HCl gas was passed until this solution was saturated. The title compound 9b, as hydrochloride, was isolated by suction filtration (0.514 g, 60% yield).

$^1$H-NMR (DMSO-d$_6$) δ: 0.81(d, 3H, J=6.29, —CH$_3$), 4.20(m, 1H, —CH), 4.67–4.85(ABq, 2H, —CH$_2$), 6.83–6.93(m. 1H, Ar—H), 7.09–7.31(m, 2H, Ar—H), 7.99 (s, 1H, Het-H), 8.81(s, 1H, Het-H) ppm.

The compound 9b as hydrochloride, was dissolved in minimum amount of water and basified with ammonia to a pH of 10 and the product was extracted with ethyl acetate. The solvent was removed under reduced pressure to give compound 9b as a free base.

$^1$H-NMR (CDCl$_3$) δ: 0.97(d, 3H, J=6.39, —CH$_3$), 2.71–2.76(b, s, 1H, —OH), 4.30–4.38(m, 1H, —CH), 4.74–4.89(ABq and s merged, 3H, —CH$_2$, —OH), 6.70–6.80(m, 2H, Ar—H), 7.36–7.48(m, 1H, Ar—H), 7.82 (s, 1H, Het-H), 7.85(s, 1H, Het-H) ppm.

Method B 1H-1,2,4-Triazole (0.276 g, 4.0 mmole) was added to an ice cooled mixture of K$_2$CO$_3$ (0.553 g, 4.0 mmole) and 5 ml of N,N-dimethylformamide. The reaction mixture was slowly brought to room temperature and a solution of compound 7b (0.4 g, 2.0 mmole) in N,N-dimethylformamide (1 ml) was added and heated at 80° C. for 3 hours. The solvent was evaporated under reduced pressure and 20 g of crushed ice was added. The resulting mixture was extracted with ethyl acetate (75 ml, 25 ml). The combined organic layers were washed with water, brine and dried over Na$_2$SO$_4$. The solvent was evaporated and the residue was chromatographed on silica gel. Elution with 2% CH$_3$OH in CHCl$_3$ gave the title compound 9b as an amorphous solid (311 mg, 58%).

$^1$H-NMR (CDCl$_3$) δ: 0.97(d, 3H, J=6.39, —CH$_3$), 2.71–2.76(b, s, 1H, —OH), 4.30–4.38(m, 1H, —CH), 4.74–4.89(ABq and s merged, 3H, —CH$_2$, —OH), 6.70–6.80(m, 2H, Ar—H), 7.36–7.48(m, 1H, Ar—H), 7.82 (s, 1H, Het-H), 7.85(s, 1H, Het-H) ppm.

Example 9
(3R)-2-(2,4-Difluorophenyl)-3-(3,4,5,6-tetrahydro-2H-pyran-2-yloxy)-1-butene [5b]

A mechanically stirred mixture of methyl triphenylphosphonium bromide (84.6 g, 0.237 moles) in 175 ml of dry tetrahydrofuran was cooled to 8° C. A solution of lithium bis(trimethylsilyl)amide (42.4 g, 0.253 moles) in 250 ml tetrahydrofuran was added to the above mixture at a rate so that the temperature of the mixture remained 23° C. After stirring for 1 hour at room temperature the contents were cooled to −70° C. and stirred for ½ hour. Added a solution of compound 4b, (2R)-2',4'-Difluoro-2-(3,4,5,6-tetrahydro-2H-pyran-2-yloxy)propiophenone (50 g, 0.185 moles) in 125 ml of tetrahydrofuran slowly to maintain the temperature of the mixture below −70° C. The resulting mixture was stirred at 7° C. for 60 hours. Added 33 ml of ethyl acetate to the above mixture followed by the addition of 2 L of hexane and allowed to stand for 15 minutes. The solid was removed by suction-filtration and washed thoroughly with 325 ml of hexane. The filtrate was washed with 1:1 mixture of methanol : water (2×650 ml) and brine (650 ml) and dried over $MgSO_4$. The solvent was evaporated to give the title compound 5b as an oil (47.7 g, 96%).

$^1$H-NMR (CDCl$_3$) δ: 1.20(d, 3H, J=6.5 Hz, —CH$_3$), 1.48–1.85(m, 6H), 3.34–3.53(m, 1H), 3.63–3.93(m, 1H), 4.58(q, 1H, J=6.5 Hz, —CH), 4.69–4.79(m, 1H), 5.15(m, 1H), 5.51(d, 1H), 6.68–6.83(m, 2H, Ar—H), 7.09–7.28 (m, 1H, Ar—H) ppm.

Example 10
(2R)-3-(2,4-Difluorophenyl)-3-buten-2-ol [6b]

A mixture of compound 5b, (3R)-2-(2,4-Difluorphenyl)-3-(3,4,5,6-tetrahydro-2H-pyran-2-yloxy)-1-butene, (40 g, 0.149 mole) and pyridinium-p-toluenesulfonate (24.61 g, 0.098 more) in 400 ml of ethanol was heated at 60° C. for 14.5 hours. The reaction mixture was concentrated in vacuo and co-evaporated with toluene. Toluene was then added to the residue and the resulting solid was removed by filtration. The filtrate was evaporated under reduced pressure and the residue was chromatographed on silica gel. Elution with 10% ethyl acetate in hexane gave the title compound 6b as light yellow oil (14.68 g, 53%).

$^1$H-NMR (CDCl$_3$) δ: 1.26(d, 3H, J=6.37, —CH$_3$), 1.80(b, 1H, —OH), 4.70(m, 1H, —CH), 5.18(s, 1H, =CH$_2$), 5.55(s, 1H, =CH$_2$), 6.77–6.89(m, 2H, Ar—H), 7.17–7.29(m, 1H, Ar—H)-ppm.

Example 11
(2R,3S)-3-(2,4-Difluorophenyl)-3,4-epoxy-2-butanol [7c]

To a solution of diethyl L-(+)-tartrate (4.86 g, 0.0236 mole) in 940 ml of dry CH$_2$Cl$_2$ were added 12 g of activated 3A° molecular sieve powder and cooled the mixture to −5° C. Added a solution of titanium (IV) isopropoxide (14.4 g, .0506 mole) in 76 ml of CH$_2$Cl$_2$ followed by t-butyl hydroperoxide (22.4 g, 0.248 mole) in 150 ml of CH$_2$Cl$_2$ and continue to stir at −5° C. for 25 minutes. To this mixture, a solution of compound 6b, (2R)-3-(2,4-Difluorophenyl)-3-buten-2-ol, (15 g, 0.0815 moles) in 76 ml of CH$_2$Cl$_2$ was added and stirred for 12 hours at 5° C. Cooled the reaction mixture to −40° C., added 4(0 ml of 30% aq. NaOH solution saturated with NaCl and the mixture was allowed to warm to 10° C. Added 40 g of MgSO$_4$, 12 g of celite and continued to stir at 10° C. for 30 minutes. The mixture was suction-filtered over celite. To the filtrate 560 ml of toluene, 450 ml of ether were added and insoluble material removed by filtration. The filtrate was evaporated in vacuo, the residue was dissolved in 400 ml of ether and suction filtered to remove the insoluble material. The filtrate was passed through a bed of silica gel and washed the pad of silica gel with 40 ml of ether. The filtrate was concentrated under reduced pressure to give yellow oil, which was chromatographed on silica gel. Elution with CHCl$_3$ gave title compound 7c as oil (11.9 g, 73%).

$^1$H-NMR (CDCl$_3$) δ: 1.20(d, 3H, J=6.21, CH$_3$), 2.66(b, 1H, —OH), 2.90–2.95(m, 1H, epoxide), 3.28–3.32(m, 1H, epoxide), 4.08–4.14(m, 1H, —CH), 6.78–6.95(m, 2H, Ar—H), 7.32–7.44(m, 1H, Ar—H) ppm.

Example 12
(2S,3R)-2-(2,4-Difluorophenyl)-1-(1H-1,2,4-triazol-1-yl)-2,3-butanediol [9c]

To an ice cooled suspension of anhydrous K$_2$CO$_3$ (0.691 g, 0.005 mole) in N,N-dimethylformamide (7 ml), 1H-1,2,4-triazole (0.345, 0.005 mole) was added in small portions under art atmosphere of nitrogen. The mixture was slowly brought to room temperature and a solution of compound 7c (2R, 3S)-3-(2,4-Difluorophenyl)-3,4-epoxy-2-butanol (0.5 g, 0.0025 mole) in N,N-dimethylformamide (1 ml) was added. The resulting mixture was heated at 80° C. for 2 hours. The solvent was removed under reduced pressure and 25 g of crushed ice was added to the residue. The so formed mixture was extracted with ethyl acetate (50 ml, 2×25 ml). The combined organic layers were washed with water (10 ml) brine (25 ml) and dried over MgSO$_4$. The solvent was removed in vacuo and the residue was chromatographed on silica gel. Elution with methanol in chloroform (0% −3%) gave the title compound 9c as an amorphous solid (0.26 g, 38%).

$^1$H-NMR (CDCl$_3$) δ: 1.25(d, 3H, J=6.26, —CH$_3$), 2.92(b, s, 1H, —OH), 4.01(m, 1H, —CH), 4.52–4.59(m, 1H), 4.99–5.05(m, 2H), 6.67–6.83(m, 2H, Ar—H), 7.46–7.59(m, 1H, Ar—H), 7.73(s, 1H, Het-H), 8.02(s, 1H, Het-H) ppm.

Example 13
(2S, 3S)-3-(2,4-difluorophenyl)-3,4-epoxybutyl 4'-nitrobenzoate [8c]

A solution of compound 7c, (1.0 g, 0.005 mole), triphenylphosphine (1.6 g, 0.006 mole), and p-nitrobenzoic acid (1.0 g, 0.006 mole) in 20 ml of dry tetrahydrofuran was cooled to 0° C. Into this clear solution, diethyl azodicarboxylate (0.94 ml, 0.006 mole) was dropped slowly and the resulting mixture was stirred for 1 hour at 0° C. The solvent was evaporated under reduced pressure and the residue was partitioned between ethylacetate (50 ml) and water (10 ml). The organic phase was washed with water, brine and dried over sodium sulfate. After filtration, the solvent was evaporated and the residue was chromatographed on silica gel column. Elution with 20% hexane in chloroform gave the (2S, 3S)-(2,4-difluorophenyl)-3,4-epoxybutyl-4'nitrobenzoate [8c]as a light yellow solid (1.01 g, 58% yield).

$^1$H-NMR (CDCl$_3$) δ: 1.40(d, 3H, J=6.57 Hz, —CH$_3$), 2.94(d, 1H, J=4.9 Hz, epoxide), 3.23(d, 1H, J=4.9 Hz, epoxide) 5.40(q, 1H, —CH), 6.81–7.00(m, 2H, Ar—H), 7.43–7.55(m, 1H, Ar—H), 8.16–8.33(m, 4H, Ar—H) ppm.

Example 14
(2S, 3S)-3-(2,4-difluorophenyl)-3,4-epoxybutyl benzoate [8d]

To an ice cooled solution of, (2.3 g, 11.5 mmole) in 20 ml of tetrahydrofuran, triphenylphosphine (3.47 g, 13.23 mmole), benzoic acid (1.61 g, 13.22 mmole), diethyl azodicarboxylate (2.3 g, 13.22 mmole) were added and stirred for 17 hours under N$_2$ at room temperature,. The reaction mixture was diluted with ethyl acetate (70 ml) and washed with water (40 ml). The aqueous phase was extracted with ethyl acetate (2×20 ml). The combined organic layers were washed with water (20 ml), brine and dried over MgSO$_4$. The solvent was evaporated and the oily residue was chromatographed on silica gel. Elution with 4% ethyl acetate in hexane gave the title compound 8d as an oil (1.40 g, 40%).

$^1$H-NMR (CDCl$_3$) δ: 1.38(d, 3H, J=6.57, —CH$_3$), 2.90(d, 1H, J=4.89 Hz, epoxide), 3.24(d, 1H, J=4.94 Hz, epoxide) 5.40(q, 1H, —CH), 6.80–6.99(m, 2H, Ar—H), 7.40–7.61(m, 4H, Ar—H) 794–8.05(m, 2H, Ar—H) ppm.

Example 15
(2S,3S)-3-(2,4-Difluorophenyl)-3,4-epoxy-2-butanol [7d]
Method A

Into an ice cooled solution of NaOCH$_3$ (174 mg, 3.2 mmole) in 20 ml of CH$_3$OH was dropped a solution of compound 8c, (2S, 3 S)-3-(2,4-difluorophenyl)-3,4-epoxybutyl 4'-nitrobenzoate (0.874 g, 2.5 mmole) in 5 ml of CH$_3$OH and the resulting mixture stirred for 1 hour at 0° C. The solvent was evaporated under reduced pressure and 10 g of crushed ice was added to the residue. The mixture was extracted with ethyl acetate (2×40 ml). The combined organic layers were washed with water (10 ml), brine and dried over MgSO$_4$. After filtration the solvent was evaporated and the residue was chromatographed on silica gel. Elution with CHCl$_3$ gave the title compound 7d as an oil (425 mg, 85%).

$^1$H-NMR (CDCl$_3$) δ: 1.17(d, 3H, J=6.55, —CH$_3$), 2.17(b, s, 1H, —OH), 2.80(d, 1H, J=5.30, epoxide), 3.30(d, 1H, J=5.24, epoxide), 4.06–4.14(m, 1H, —CH), 6.76–6.94(m, 2H, Ar—H), 7.36–7.48(m, 1H, Ar—H) ppm.

Method B

To an ice cooled solution of NaOCH$_3$ (277 mg, 5.16 mmole) in 40 ml of CH$_3$OH was dropped a solution of compound 8d, (2S,3S)-3-(2,4-difluorophenyl)-3,4-epoxybutyl benzoate (1.2 g, 3.96 mmole) in 10 ml of CH$_3$OH and the resulting mixture stirred for 2 hours ar. room temperature. The solvent was evaporated under reduced pressure and 20 g of crushed ice added to the residue. The solution was acidified with 1N HCl and extracted with ethyl acetate (2×50 ml). The combined organic layer was washed with saturated NaHCO$_3$ (2×20 ml), water, brine and dried over MgSO$_4$. The solvent was evaporated and the residue was chromatographed on silica gel. Elution with CHCl$_3$ gave the title compound 7d as an oil (600 mg, 76%).

$^1$H-NMR (CDCl$_3$) δ: 1.17(d, 3H, J=6.55, —CH$_3$), 2.17(b, s, 1H, —OH), 2.80(d, 11, J=5.30, epoxide), 3.30(d, 1H, J=5.24, epoxide), 4.06–4.14(m, 1H, —CH), 6.76–6.94(m, 2H, Ar—H), 7.36–7.48(m, 1H, Ar—H) ppm.

Example 16
(2S,3S)-2-(2,4-Difluorophenyl)-1-(1H-1,2,4-triazol-1-yl)-2,3-butanediol [9d]
Method A A solution of compound 7d (392 mg, 2.0 mmole) in 15 ml of dry acetonitrile were added potassium carbonate (813 mg, 5.9 mmole) and 1,2,4-triazole (406 mg, 5.9 mmole). The resulting mixture was refluxed for 4 hour under nitrogen. After cooling, the solid was removed by suction filtration and washed with small amounts of ethylacetate. The filtrate was concentrated under reduced pressure and the residue was dissolved in 30 ml of ethylacetate. The resulting solution was washed with water (2×5 ml), brine and the organic phase was dried over sodium sulfate. The contents were suction filtered and the filtrate was diluted with 30 ml of diethyl ether. The solution was cooled and a steady stream of anhydrous HCl gas was passed until this solution was saturated. The title compound 9d, as hydrochloride, was isolated by suction filtration (0.350 g, 57% yield).

$^1$H-NMR (DMSO-d$_5$) δ: 0.81(d, 3H, J=6.29, —CH$_3$), 4.20(m, 1H, —CH), 4.67–4.85(ABq, 2H, —CH,), 6.83–6.93 (m, 1H, Ar—H), 7.09–7.31(m, 2H, Ar—H), 7.99(s, 1H, Het-H), 8.81(s, 1H, Het-H) ppm.

The compound 9d, as hydrochloride, was dissolved in minimum amount of water and basified with ammonia to a pH of 10 and the product extracted with ethyl acetate. The solvent was removed under reduced pressure to give compound 9d as a free base.

$^1$H-NMR (CDCl$_3$) δ: 0.97(d, 3H, J=6.39, —CH$_3$), 2.71–2.76(b, s, 1H, —OH), 4.30–4.38(m, 1H, —CH), 4.74–4.89(ABq and s merged, 3H, —CH$_2$, —OH), 6.70–6.80(m, 2H, Ar—H), 7.36–7.48(m, 1H, Ar—H), 7.82 (s, 1H, Het-H), 7.85(s, 1H, Het-H) ppm.

Method B 1H-1,2,4-Triazole (0.304 g, 4.4 mmole) was added to an ice cooled mixture of K$_2$CO$_3$ (0.608 g, 4.4 mmole) and 5 ml of N,N-dimethylformamide. The reaction mixture was slowly brought to room temperature and a solution of compound 7d (0.44 g, 2.2 mmole) in N,N-dimethylformamide (1 ml) was added and heated at 80° C. for 3 hours. The solvent was evaporated under reduced pressure and 20 g of crushed ice was added. The resulting mixture was extracted with ethyl acetate (75 ml, 25 ml). The combined organic layers were washed with water, brine and dried over Na$_2$SO$_4$. The solvent was evaporated and the residue was chromatographed on silica gel. Elution with 2% CH$_3$OH in CHCl$_3$ gave the title compound 9d as an amorphous solid (342 mg, 58%).

$^1$H-NMR (CDCl$_3$) δ: 0.97(d, 3H, J=6.39, —CH$_3$), 2.71–2.76(b, s, 1H, —OH), 4.30–4.38(m, 1H, —CH), 4.74–4.89(ABq and s merged, 3H, —CH$_2$, —OH), 6.70–6.80(m, 2H, Ar—H), 7.36–7.48(m, 1H, Ar—H), 7.82 (s, 1H, Het-H), 7.85(s, 1H, Het-H) ppm.

Example 17
Preparation of (2R,3R)-2-(2,4-Difluorophenyl)-1-(1H-1,2,4-triazol-1-yl)-2,3-butanediol [9b] from 7a in one pot A solution of compound 7a, (2S, 3R)-3-(2,4-Difluorophenyl)-3,4-epoxy-2-butanol (2.0 g, 0.01 mole), triphenylphosphine (3.2 g, 0.012 mole), and benzoic acid (1.47 g, 0.012 mole) in 40 ml of dry tetrahydrofuran was cooled to 0° C. Into this clear solution, diethyl azodicarboxylate (1.88 ml, 0.012 mole) was dropped slowly and the resulting mixture was stirred for 1 hour at 0° C. The reaction mixture, while keeping the temperature at 0° C., was diluted with 40 ml of dry methanol and a solution of sodium methoxide (1).700 g, 0.013 mole) in 20 ml of methanol was dropped into this. The contents were stirred at 0° C. for 6 hours. The solvent was evaporated and the residue was dissolved in 40 ml of dry acetonitrile followed by the addition of potassium carbonate (4.14 g, 0.030 mole) and 1,2,4-triazole (2.08 g, 0.030 mole). The resulting mixture was refluxed for 4 hour under nitrogen. After cooling, the solid was removed by suction filtration and washed with small amounts of ethylacetate. The filtrate was concentrated under reduced pressure and the residue was dissolved in 50 ml of ethylacetate. The resulting solution was washed with water (2×5 ml), brine and the organic phase was dried over sodium sulfate. The contents were suction filtered and the filtrate was diluted with 50 ml of diethyl ether. The solution was cooled and a steady stream of anhydrous HCl gas was passed until this solution was saturated. The title compound 9b, as hydrochloride, was isolated by suction filtration (0.896 g, 29% yield from compound 7a).

$^1$H-NMR (DMSO-4) δ: 0.81(d, 3H, J=6.29, —CH$_3$), 4.20(m, 1H, —CH), 4.67–4.85(ABq 2H, —CH$_2$), 6.83–6.93 (m, 1H, Ar—H), 7.09–7.31(m, 2H, Ar—H), 7.99(s, 1H, Het-H), 8.81 (s, 1 H, Het-H) ppm.

The compound 9b, as hydrochloride, was dissolved in minimum amount of water and basified with ammonia to a pH of 10, extracted with ethyl acetate. The solvent was removed under reduced pressure to give compound 9b as a free base.

$^1$H-NMR (CDCl$_3$) δ: 0.97(d, 3H, J=6.39, —CH$_3$), 2.71–2.76(b, s, 1H, —OH), 4.30–4.38(m, 1H, —CH), 4.74–4.89(ABq and s merged, 3H, —CH$_2$, —OH), 6.70–6.80(m, 2H, Ar—H), 7.36–7.48(m, 1H, Ar—H), 7.82 (s, 1H, Het-H), 7.85(s, 1H, Het-H) ppm.

Example 18

Large Scale Preparation of (2R,3R)-2-(2,4-Difluorophenyl)-1-(1H-1,2,4-triazol-1-yl)-2,3-butanediol [9b] from 7a in one pot A solution of compound 7a (500 g, 2.5 mole), triphenylphosphine (787 g, 3.0 mole), and p-nitrobenzoic acid (501 g, 3.0 mole) in 8 L of dry tetrahydrofuran was cooled to 0° C. Into this clear solution, diethyl azodicarboxylate (472 ml, 3.0 mole) was dropped slowly and the resulting mixture was stiffed for 1 hour at 0° C. The reaction mixture, while keeping the temperature at 0° C., was diluted with 5 L of dry methanol and a solution of sodium methoxide (176 g, 3.25 mole) in 3 L of methanol was dropped into this. The contents were stirred at 0° C. for 2 hours. The solvent was evaporated and to the residue was 8 L of dry acetonitrile followed by the addition of potassium carbonate (1037 g, 7.5 mole) and 1,2,4-triazole (518 g, 7.5 mole). The resulting mixture was refluxed for 4 hour under nitrogen. After cooling, the solid was removed by suction filtration and washed with ethylacetate (2×1 L). The fine solid from the filtrate was removed over a bed of celite. The filtrate was concentrated under reduced pressure and the residue was dissolved in 8 L of ethylacetate. The resulting solution was washed with water (2×1 L), brine and the organic phase was dried over sodium sulfate. The contents were suction filtered and the filtrate. The solution was cooled and a steady stream of anhydrous HCl gas was passed until this solution was saturated. The title compound 9b, as hydrochloride, was isolated by suction filtration (300 g, 39% yield from compound 7a).

$^1$H-NMR (DMSO-d$_6$) δ: 0.81 (d, 3H, J=6.29, —CH$_3$), 4.20(m, H, —CH), 4.67–4.85(ABq, 2H, —CH$_2$), 6.83–6.1)3(m, 1H, Ar—H), 7.09–7.31(m, 2H, Ar—H), 7.99(s, 1H, Het-H), 8.81(s, 1H, Het-H) ppm.

The compound 9b, as hydrochloride, was dissolved in minimum amount of water and basified with ammonia to a pH of 10. The solvent was removed under reduced pressure to give compound 9b as a free base.

$^1$H-NMR (CDCl$_3$) δ: 0.97(d, 3H, J=6.39, —CH$_3$), 2.71–2.76(b, s, 1H, —OH), 4.30–4.38(m, 1H, —CH), 4.74–4.89(ABq and s merged, 3H, —CH$_2$, —OH), 6.70–6.80(m, 2H, Ar—H), 7.36–7.48(m, 1H, Ar—H), 7.82 (s, 1H, Het-H), 7.85(s, 1H, Het-H) ppm.

Example 19

Preparation of (2S,3S)-2-(2,4-Difluorophenyl)-1-(1H-1,2,4-triazol-1-yl)-2,3-butanediol [9d] from 7c in one pot Method A A solution of compound 7c (1.0 g, 0.005 mole), triphenylphosphine (1.6 g, 0.006 mole), and benzoic acid (0.733 g, 0.006 mole) in 20 ml of dry tetrahydrofuran was cooled to 0° C. Into this clear solution, diethyl azodicarboxylate (0.94 ml, 0.006 mole) was dropped slowly and the resulting mixture was stirred for 1 hour at 0° C. The reaction mixture, while keeping the temperature at 0° C., was diluted with 20 ml of dry methanol and a solution of sodium methoxide (0.351 g, 0.0065 mole) in 10 ml of methanol was dropped into it. The contents were stirred at 0° C. for 6 hours. The solvent was evaporated and the residue was dissolved in 20 ml of dry acetonitrile followed by the addition of potassium carbonate (2.07 g, 0.015 mole) and 1,2,4-triazole (1.04 g, 0.015 mole). The resulting mixture was refluxed for 4 hour under nitrogen. After cooling, the solid was removed by suction filtration and washed with small amounts of ethylacetate. The filtrate was concentrated under reduced pressure and the residue was dissolved in 50 ml of ethylacetate. The resulting solution was washed with water (2×5 ml), brine and the organic phase was dried over sodium sulfate. The contents were suction filtered and the filtrate was diluted with 50 ml of diethyl ether. The solution was cooled and a steady stream of anhydrous HCl gas was passed until this solution was saturated. The title compound 9d, as hydrochloride, was isolated by suction filtration (0.430 g, 28% yield from compound 7c).

$^1$H-NMR (DMSO-d$_6$) δ: 0.81 (d, 3H, J=6.29, —CH$_3$), 4.20(m, 1H, —CH), 4.67–4.85(ABq 2H, —CH$_2$), 6.83–6.93 (m, 1H, Ar—H), 7.09–7.31(m, 2H, Ar—H), 7.99(s, 1H, Het-H), 8.81(s, 1H, Het-H) ppm.

The compound 9d, as hydrochloride, was dissolved in minimum amount of water and basified with ammonia to a pH of 10 and extracted with ethyl acetate. The solvent was removed under reduced pressure to give compound 9d as a free base.

$^1$H-NMR (CDCl$_3$) δ: 0.97(d, 3H, J=6.39, —CH$_3$), 2.71–2.76(b, s, 1H, —OH), 4.30–4.38(m, 1H, —CH), 4.74–4.89(ABq and s merged, 3H, —CH$_2$, —OH), 6.70–6.80(m, 2H, Ar—H), 7.36–7.48(m, 1H, Ar—H), 7.82 (s, 1H, Het-H), 7.85(s, 1H, Het-H) ppm.

Method B

A solution of compound 7c (5.0 g, 0.025 mole), triphenylphosphine (7.87 g, 0.030 mole), and p-nitrobenzoic acid (5.01 g, 0.030 mole) in 80 ml of dry tetrahydrofuran was cooled to 0° C. Into this clear solution, diethyl azodicarboxylate (4.7 ml, 0.030 mole) was dropped slowly and the resulting mixture was stirred for 1 hour at 0° C. The reaction progress was monitored by TLC. The reaction mixture, while keeping the temperature at 0° C., was diluted with 50 ml of dry methanol and a solution of sodium methoxide (1.76 g, 0.0325 mole) in 30 ml of methanol was dropped into this. The contents were stirred at 0° C. for 2 hours. The solvent was evaporated and to the residue was 100 ml of dry acetonitrile followed by the addition of potassium carbonate (10.4 g, 0.075 mole) and 1,2,4-triazole (5.18 g, 0.075 mole). The resulting mixture was refluxed for 4 hour under nitrogen. After cooling, the solid was removed by suction filtration and washed with ethylacetate (2×25 ml). The fine solid from the filtrate was removed over a bed of celite. The filtrate was concentrated under reduced pressure and the residue was dissolved in 150 ml of ethylacetate. The resulting solution was washed with water (2×25 ml), brine and the organic phase was dried over sodium sulfate. The contents were suction filtered and the filtrate was diluted with 150 ml of diethyl ether. The solution was cooled and a steady stream of anhydrous HCl gas was passed until this solution was saturated. The title compound 9d, as hydrochloride, was isolated by suction filtration (2.90 g, 38% yield from compound 7c).

$^1$H-NMR (DMSO-d$_6$) δ: 0.81 (d, 3H., J=6.29, —CH$_3$), 4.20(m, 1H, —CH), 4.67–4.85(ABq, 2H, —CH$_2$), 6.83–6.93(m, 1H, Ar—H), 7.09–7.31(m, 2H, Ar—H), 7.99 (s, 1H, Het-H), 8.81(s, 1H, Het-H) ppm.

The compound 9d, as hydrochloride, was dissolved in minimum amount of water and basified with ammonia to a pH of 10. The product was extracted with ethyl acetate. The solvent was removed under reduced pressure to give compound 9d as a free base.

$^1$H-NMR (CDCl$_3$) δ: 0.97(d, 3H, J=6.39, —CH$_3$), 2.71–2.76(b, s, 1H, —OH), 4.30–4.38(m, 1H, —CH), 4.74–4.89(ABq and s merged, 3H, —CH$_2$, —OH), 6.70–6.80(m, 2H, Ar—H), 7.36–7.48(mn, 1H, Ar—H), 7.82 (s, 1H, Het-H), 7.85(s, 1H, Het-H) ppm.

Example 20
Large Scale Preparation of (2R,3R)-2-(2,4-Difluorophenyl)-1-(1H-1,2,4-triazol-1-yl)-2,3-butanediol [9b] from methyl-S-(–)-lactate 1a A mixture of methyl (S)-(–) lactate (500 g, 4.803 mole) and morpholine (1.3 L, 14.9 mole) was heated at 85° C., under N$_2$, for 70 hours. The solvent was removed under reduced pressure. The contents were diluted with 6 L of dichloromethane and washed (4×250 ml) with a mixture of 10% HCl in brine. The organic phase was dried over sodium sulfate and evaporated under reduced pressure to give the a pale yellow oil (571.5 g). This pale yellow oil (571.5 g) was diluted with dichloromethane (1.9 L) followed by the addition of p-toluene sulfonic acid (6.82 g, 0.0359 mole). The solution was cooled 0° C. and into it 3,4-dihydro-2H-pyran (393 ml, 4.311 mole) was dropped slowly over a period of 1 hour. After stirring for another 15 minutes the solvent was removed under reduced pressure to give pale yellow oil, 3a (859 g).

A mixture of magnesium (103.1 g, 4.24 mole) and 1-bromo-2,4-difluorobenzene (50 ml, 0.44 mole) in tetrahydrofuran (3.5 L) were vigorously stirred and warmed to 40° C. to initiate the reaction. The contents were kept at 40° C. with the gradual addition of 1-bromo-2,4-difluorobenzene (429 ml, 3.80 mole). The contents were stirred at room temperature for 1.5 hour and then cooled to –20° C. A solution of the oil 3a (859 g) in dry tetrahydrofuran (500 ml) was dropped over a period of 1 hour into the cooled solution. The mixture was stirred at room temperature for additional 3.5 hours, diluted with ethyl acetate (4.6 L), then a 1:1 mixture of brine and saturated aqueous NH$_4$Cl (4.6 L) was added. The aqueous layer was removed and extracted with ethylacetate (3×2 L). The combined organic phases were washed with water (2 L), brine (2 L) and dried over Na$_2$SO$_4$. The solvent was removed under reduced pressure to give the crude 4a as a dark brown oil (967 g).

A mechanically stirred mixture of methyl triphenylphosphonium bromide (1616 g, 4.52 moles) in dry tetrahydrofuran (3.5 L) was cooled to 8° C. A solution of lithium bis (trimethylsilyl)amide (810 g, 4.84 moles) in tetrahydrofuran (5 L) was added to the above mixture at a rate so that the temperature of the mixture remained at 23° C. After stirring for 1 hour at room temperature the contents were cooled to –70 ° C. and stirred for ½ hour. Added a solution of compound 4a, (967 g) in tetrahydrofuran (2.5 L) slowly to maintain the temperature of the mixture below –70 ° C. The resulting mixture was stirred at 7° C. for 17 hours. Added 550 ml of ethyl acetate to the above mixture followed by the addition of hexane (3.9 L) and allowed standing for 15 minutes. The solid was removed by suction-filtration and washed thoroughly with hexane (3 L). The filtrate was washed with 1:1 mixture of methanol:water (2×10 L), brine and dried over MgSO$_4$. The solvent was evaporated to give the crude 5a as an oil (870).

A mixture of crude 5a, (870) and pyridinium-p-toluenesulfonate (350 g, 1.39 mole) in ethanol (12 L) was heated at 60° C. for 9 hours. The reaction mixture was concentrated in vacuo and co-evaporated with toluene. The residue was diluted with toluene and the resulting solid was removed by filtration. The filtrate was evaporated under reduced pressure to give the crude 6a as light brown oil (664 g).

To a solution of diethyl L(+)-tartrate (161 ml, 0.94 mole) in dry CH$_2$Cl$_2$ (24 L) was added activated 3A° molecular sieve powder (600 g) and cooled the mixture to –5° C. Added a solution of titanium (IV) isopropoxide (597 ml, 2.0 mole) followed by t-butyl hydroperoxide (1.56 L of 5–6M solution in decane) and continue to stir at –5° C. for 25 minutes. To this mixture, a solution of crude 6a, (664 g) in CH$_2$Cl$_2$ (2 L) was added and stirred for 12 hours at 5° C. Cooled the reaction mixture to –40° C., added 1.4 L of 30% aq. NaOH solution saturated with NaCl and the mixture was allowed to warm to 10° C. Added 1.2 kg of MgSO$_4$, 400 g of celite and continued to stir at 10° C. for 30 minutes. The mixture was suction-filtered over celite. To the filtrate toluene (20 L), and 15 L of ether were added and insoluble material removed by filtration. The filtrate was evaporated under reduced pressure to give the crude 7a as a light brown oil (740 g).

A solution of crude 7 (740 g), triphenylphosphine (1165 g, 4.44 mole), and p-nitrobenzoic acid (742 g, 4.44 mole) in 8 L of dry tetrahydrofuran was cooled to 0 ° C. Into this clear solution, diethyl azodicarboxylate (698 ml, 4.43 mole) was dropped slowly and the resulting mixture was stirred for 1 hour at 0° C. The reaction mixture, while keeping the temperature at 0° C., was diluted with 5 L of dry methanol and a solution of sodium methoxide (260 g, 4.81 mole) in methanol (3 L) was dropped into this. The contents were stirred at 0° C. for 2 hours. The solvent was evaporated and the residue was dissolved in 8 L of dry acetonitrile followed by the addition of potassium carbonate (1 534 g, 11.1 mole) and 1,2,4-triazole (767 g, 11.1 mole). The resulting mixture was refluxed for 4 hour under nitrogen. After cooling, the solid was removed by suction filtration and washed with ethylacetate (2×1 L). The fine solid from the filtrate was removed over a bed of celite. The filtrate was concentrated under reduced pressure and the residue was dissolved in 8 L of ethylacetate. The resulting solution was washed with water (2×1 L), brine and the organic phase was dried over sodium sulfate. The contents were suction filtered. The filterate was cooled and a steady stream of anhydrous HCl gas was passed until this solution was saturated. The title compound 9b, as hydrochloride, was isolated by suction filtration.

$^1$H-NMR (DMSO-d$_6$) δ: 0.81 (d, 3H, J=6.29, —CH$_3$), 4.20(m, 1 H, —CH), 4.67–4.85(ABq, 2H, —CH$_2$), 6.83–6.93(m, 1H, Ar—H), 7.09–7.31(m, 2H, Ar—H), 7.99 (s, 1H, Het-H), 8.81 (s, 1H, Het-H) ppm.

Example 21
Preparation of (2R,3S)-2-(2,4-Difluorophenyl)-1-(1H-1,2,4-triazol-1-yl)-2,3-butanediol [9a] from methyl-S-(–)-lactate 1a A mixture of methyl (S)-(–) lactate (10 g, 0.96 mole) and morpholine (260 ml, 2.98 mole) is heated at 85° C., under N$_2$, for 70 hours. The solvent is removed under reduced pressure. The contents are diluted with 120 ml of dichloromethane and washed (4×50 ml) with a mixture of 10% HCl in brine. The organic phase is dried over sodium sulfate and evaporated under reduced pressure to give yellow oil . This pale yellow oil is diluted with dichloromethane (280 ml) followed by the addition of p-toluene sulfonic acid (1.36 g, 0.007 mole). The solution is cooled 0° C. and into it 3,4-dihydro-2H-pyran (79 ml, 0.86 mole) is dropped slowly over a period of 1 hour. After stirring for another 15 minutes the solvent is removed under reduced pressure to give pale yellow oil, 3a.

A mixture of magnesium (20.6 g, 0.848 mole) and 1-bromo-2,4-difluorobenzene (10 ml, 0.088 mole) in tetrahydrofuran (700 ml) are vigorously stirred and warmed to 40° C. to initiate the reaction. The contents are kept at 40° C. with the gradual addition of 1-bromo-2,4-difluorobenzene (89 ml, 0.76 mole). The contents are stirred at room temperature for 1.5 hour and then cooled to −20° C. A solution of the oil 3a in dry tetrahydrofuran (100 ml) is dropped over a period of 1 hour into the cooled solution. The mixture is stirred at room temperature for additional 3.5 hours, diluted with ethyl acetate (900 ml), then a 1:1 mixture of brine and saturated aqueous $NH_4Cl$ (900 ml) is added. The aqueous layer is removed and extracted with ethylacetate (3×400 ml). The combined organic phases are washed with water (400 ml), brine (400 ml) and dried over $Na_2SO_4$. The solvent is removed under reduced pressure to give the crude 4a as oil.

A mechanically stirred mixture of methyl triphenylphosphonium bromide (323 g, 0.904 moles) in dry tetrahydrofuran (700 ml) is cooled to 8° C. A solution of lithium bis(trimethylsilyl)amide (162 g, 0.904 moles) in tetrahydrofuran (1 L) is added to the above mixture at a rate so that the temperature of the mixture remained at 23 ° C. After stirring for 1 hour at room temperature the contents are cooled to −70° C. and stirred for ½ hour. Added a solution of compound 4a in tetrahydrofuran (500 ml) slowly to maintain the temperature of the mixture below −70° C. The resulting mixture is stirred at 7° C. for 17 hours. Added 100 ml of ethyl acetate to the above mixture followed by the addition of hexane (800 ml) and allowed standing for 15 minutes. The solid is removed by suction-filtration and washed thoroughly with hexane (600 ml). The filtrate is washed with 1:1 mixture of methanol:water (2×200 ml), brine and dried over $MgSO_4$. The solvent is evaporated to give the crude 5a as oil.

A mixture of crude 5a and pyridinium-p-toluenesulfonate (70 g, 0.278mole) in ethanol (250 ml) is heated at 60° C. for 9 hours. The reaction mixture is concentrated in vacuo and co-evaporated with toluene. The residue is diluted with toluene and the resulting solid is removed by filtration. The filtrate is evaporated under reduced pressure to give the crude 6a as light brown oil.

To a solution of diethyl L(+)-tartrate (32.2 ml, 0.188 mole) in dry $CH_2Cl_2$ (5 L) is added activated 3A° molecular sieve powder (120 g) and cooled the mixture to −5 ° C. Added a solution of titanium (IV) isopropoxide (120 ml, 0.4 mole) followed by t-butyl hydroperoxide (312 ml of 5–6M solution in decane) and continue to stir at −5 ° C. for 25 minutes. To this mixture, a solution of crude 6a in $CH_2Cl_2$ (400 ml) is added and stirred for 12 hours at 5° C. Cooled the reaction mixture to −40° C., added 280 ml of 30% aq. NaOH solution saturated with NaCl and the mixture is allowed to warm to 10° C. Added 250 g of $MgSO_4$, 80 g of celite and continued to stir at 10° C. for 30 minutes. The mixture is suction-filtered over celite. To the filtrate toluene (4 L) and 3 L of ether are added and insoluble material removed by filtration. The filtrate is evaporated under reduced pressure to give the crude 7a as oil.

A solution of crude 7a in 2.0 L of dry acetonitrile are added potassium carbonate (306 g, 2.2mole) and 1,2,4-triazole (152 g, 2.2 mole). The resulting mixture is refluxed for 4 hour under nitrogen. After cooling, the solid is removed by suction filtration and washed with small amounts of ethylacetate. The filtrate is concentrated under reduced pressure and the residue is dissolved in 4.0 L of ethylacetate. The resulting solution is washed with water (2×1000 ml), brine and the organic phase is dried over sodium sulfate. The contents are suction filtered and the filtrate is diluted with 60 ml of diethyl ether. The solution is cooled and a steady stream of anhydrous HCl gas is passed until this solution is saturated. The saturated solution is kept under cooling for 5 hrs during which time a solid is separated. The title compound 9a, as hydrochloride, is isolated by suction filtration.

$^1$H-NMR ($CDCl_3$) δ: 1.25(d, 3H, J=6.44, —$CH_3$), 2.89(b, s, 1H, —OH), 4.01(m, 1H, —CH), 4.51–4.58(m, 1H), 4.99–5.05(m, 2H), 6.65–6.85(m, 2H, Ar—H), 7.47–7.59(m, 1H, Ar—H), 7.73(s, 1H, Het-H), 8.02(s, 1H, Het-H) ppm.

Example 22

Preparation of (2S,3R)-2-(2,4-Difluorophenyl)-1-(1H-1,2,4-triazol-1-yl)-2,3 -butanediol [9c] from methyl-R-(+)-lactate lb A mixture of methyl (R)-(+) lactate (25 g, 0.24 mole) and morpholine (65 ml, 0.075 mole) is heated at 85° C., under $N_2$, for 70 hours. The solvent is removed under reduced pressure. The contents are diluted with 600 ml of dichloromethane and washed (4×15 ml) with a mixture of 10% HCl in brine. The organic phase is dried over sodium sulfate and evaporated under reduced pressure to give the a yellow oil. This pale yellow oil is diluted with dichloromethane (90 ml) followed by the addition of p-toluene sulfonic acid (340 mg, 0.0018 mole). The solution is cooled 0° C. and into it 3,4-dihydro-2H-pyran (20 ml, 0.21 mole) is dropped slowly over a period of 1 hour. After stirring for another 15 minutes the solvent is removed under reduced pressure to give pale yellow oil, 3b.

A mixture of magnesium (5.15 g, 0.0.21 mole) and 1-bromo-2,4-difluorobenzene (25 ml, 0.022 mole) in tetrahydrofuran (170 ml) are vigorously stirred and warmed to 40° C. to initiate the reaction. The contents are kept at 40° C. with the gradual addition of 1-bromo-2,4-difluorobenzene (22 ml, 0.19 mole). The contents are stirred at room temperature for 1.5 hour and then cooled to −20° C. A solution of the oil 3a in dry tetrahydrofuran (25 ml) is dropped over a period of 1 hour into the cooled solution. The mixture is stirred at room temperature for additional 3.5 hours, diluted with ethyl acetate (200 ml), then a 1:1 mixture of brine and saturated aqueous $NH_4Cl$ (200 ml) is added. The aqueous layer is removed and extracted with ethylacetate (3×100 ml). The combined organic phases are washed with water (100 ml), brine (100 ml) and dried over $Na_2SO_4$. The solvent is removed under reduced pressure to give the crude 4b as a dark brown oil.

A mechanically stirred mixture of methyl triphenylphosphonium bromide (80.5 g, 0.226 moles) in dry tetrahydrofuran (180 ml) is cooled to 8° C. A solution of lithium bis(trimethylsilyl)amide (40.5 g, 0.24 moles) in tetrahydrofuran (200 ml) is added to the above mixture at a rate so that the temperature of the mixture remained at 23° C. After stirring for 1 hour at room temperature the contents are cooled to −70 ° C. and stirred for ½ hour. Added a solution of compound 4b, obtained above, in tetrahydrofuran (120 ml) slowly to maintain the temperature of the mixture below −70 ° C. The resulting mixture is stirred at 7° C. for 17 hours. Added 25 ml of ethyl acetate to the above mixture followed by the addition of hexane (200 ml) and allowed standing for 15 minutes. The solid is removed by suction-filtration and washed thoroughly with hexane (150nit). The filtrate is washed with 1:1 mixture of methanol: water (2×500 ml), brine and dried over $MgSO_4$. The solvent is evaporated to give the crude 5b as an oil.

A mixture of crude 5b, and pyridinium-p-toluenesulfonate (17.5 g, 0.07 mole) in ethanol (500 ml) is heated at 60° C. for 9 hours. The reaction mixture is concentrated in vacuo and co-evaporated with toluene. The residue is diluted with toluene and the resulting solid is removed by filtration. The filtrate is evaporated under reduced pressure to give the crude 6b as light brown oil.

To a solution of diethyl L(+)-tartrate (8 ml, 0.047 mole) in dry $CH_2Cl_2$ (1.2 L) is added activated 3A° molecular sieve powder (300 g) and cooled the mixture to −5 ° C. Added a solution of titanium (IV) isopropoxide (30 ml, 0.10 mole) followed by t-butyl hydroperoxide (78 ml of 5–6M solution in decane) and continue to stir at −5° C. for 25 minutes. To this mixture, a solution of crude 6b, in $CH_2Cl_2$ (100 ml) is added and stirred for 12 hours at 5° C. Cooled the reaction mixture to −40° C., added 70 ml of 30% aq. NaOH solution saturated with NaCl and the mixture is allowed to warm to 10° C. Added 60 g of $MgSO_4$, 20 g of celite and continued to stir at 10° C. for 30 minutes. The mixture is suction-filtered over celite. To the filtrate toluene (1 L), and 700 ml of ether are added and insoluble material removed by filtration. The filtrate is evaporated under reduced pressure to give the crude 7c as a light brown oil.

A solution of crude 7c in 500 ml of dry acetonitrile are added potassium carbonate (76.5 g, 0.55 mole) and 1,2,4-triazole (38 g, 0.55 mole). The resulting mixture is refluxed for 4 hour under nitrogen. After cooling, the solid is removed by suction filtration and washed with small amounts of ethylacetate. The filtrate is concentrated under reduced pressure and the residue is dissolved in 1.0 L of ethylacetate. The resulting solution is washed with water (2×200 ml), brine and the organic phase is dried over sodium sulfate. The contents are suction filtered and the filtrate is diluted with 30 ml of diethyl ether. The solution is cooled and a steady stream of anhydrous HCl gas is passed until this solution is saturated. The saturated solution is kept under cooling for 5–10 hrs during which time a solid is separated. The title compound 9c, as hydrochloride, is isolated by suction filtration.

$^1$H-NMR (DMSO) δ: 1.25(d, 3H, J=6.26, —$CH_3$), 2.92(b, s, 1H, —OH), 4.01(m, 1H, —CH), 4.52–4.59(m, 1H), 4.99–5.05(m, 2H), 6.67–6.83(m, 2H, Ar—H), 7.46–7.59(m, 1H, Ar—H), 7.73(s, 1H, Het-H), 8.02(s, 1H, Het-H) ppm.

Example 23
Preparation of (2S,3S)-2-(2,4-Difluorophenyl)-1-(1H-1,2,4-triazol-1-yl)-2,3-butanediol [9d] from methyl-R-(+)-lactate 1b A mixture of methyl (R)-(+) lactate (50 g, 0.48 mole) and morpholine (130 ml, 0.149 mole) is heated at 85° C., under $N_2$, for 70 hours. The solvent is removed under reduced pressure. The contents are diluted with 600 ml of dichloromethane and washed (4×25 ml) with a mixture of 10% HCl in brine. The organic phase is dried over sodium sulfate and evaporated under reduced pressure to give yellow oil. This pale yellow oil is diluted with dichloromethane (190 ml) followed by the addition of p-toluene sulfonic acid (682 mg, 0.0036 mole). The solution is cooled 0° C. and into it 3,4-dihydro-2H-pyran (39 ml, 0.431 mole) is dropped slowly over a period of I hour. After stirring for another 15 minutes the solvent is removed under reduced pressure to give pale yellow oil, 3b.

A mixture of magnesium (10.3 g, 0.42 mole) and 1-bromo-2,4-difluorobenzene (50 ml, 0.044 mole) in tetrahydrofuran (350 ml) are vigorously stirred and warmed to 40° C. to initiate the reaction. The contents are kept at 40° C. with the gradual addition of 1-bromo-2,4-difluorobenzene (43 ml, 0.38 mole). The contents are stirred at room temperature for 1.5 hour and then cooled to −20° C. A solution of the oil 3b in dry tetrahydrofuran (50 ml) is dropped over a period of 1 hour into the cooled solution. The mixture is stirred at room temperature for additional 3.5 hours, diluted with ethyl acetate (450 ml), then a 1:1 mixture of brine and saturated aqueous $NH_4Cl$ (450 ml) is added. The aqueous layer is removed and extracted with ethylacetate (3×200 ml).

The combined organic phases are washed with water (200 ml), brine (200 ml) and dried over $Na_2SO_4$. The solvent is removed under reduced pressure to give the crude 4b as dark brown oil.

A mechanically stirred mixture of methyl triphenylphosphonium bromide (161 g, 0.452 moles) in, dry tetrahydrofuran (350 ml) is cooled to 8° C. A solution of lithium bis (trimethylsilyl) amide (81 g, 0.48 moles) in tetrahydrofuran (500 ml) is added to the above mixture at a rate so that the temperature of the mixture remained at 23° C. After stirring for 1 hour at room temperature the contents are cooled to −70 ° C. and stirred for ½ hour. Added a solution of crude 4b, obtained above, in tetrahydrofuran (250 ml) slowly to maintain the temperature of the mixture below −70 ° C. The resulting mixture is stirred at 7° C. for 17 hours. Added 50 ml of ethyl acetate to the above mixture followed by the addition of hexane (390 ml) and allowed standing for 15 minutes. The solid is removed by suction-filtration and washed thoroughly with hexane (300 ml). The filtrate is washed with 1:1 mixture of methanol: water (2×1 L), brine and dried over $MgSO_4$. The solvent is evaporated to give the crude 5b as an oil.

A mixture of crude 5b, and pyridinium-p-toluenesulfonate (35 g, 0.14 mole) in ethanol (1.2 L) is heated at 60° C. for 9 hours. The reaction mixture is concentrated in vacuo and co-evaporated with toluene. The residue is diluted with toluene and the resulting solid is removed by filtration. The filtrate is evaporated under reduced pressure to give the crude 6b as light brown oil.

To a solution of diethyl L(+)-tartrate (16 ml, 0.094 mole) in dry $CH_2Cl_2$ (2.4 L) is added activated 3A° molecular sieve powder (600 g) and cooled the mixture to −5° C. Added a solution of titanium (IV) isopropoxide (59 ml, 0.20 mole) followed by t-butyl hydroperoxide (156 ml of 5–6M solution in decane) and continue to stir at −5° C. for 25 minutes. To this mixture, a solution of crude 6b, in $CH_2Cl_2$ (200 ml) is added and stirred for 12 hours at 5° C. Cooled the reaction mixture to −40° C., added 140 ml of 30% aq. NaOH solution saturated with NaCl and the mixture is allowed to warm to 10 °C. Added 120 g of $MgSO_4$, 40 g of celite and continued to stir at 10° C. for 30 minutes. The mixture is suction-filtered over celite. To the filtrate toluene (2 L), and 1.5 L of ether re added and insoluble material removed by filtration. The filtrate is evaporated under reduced pressure to give the crude 7c as a light brown oil.

A solution of crude 7c triphenylphosphine (116 g, 0.44 mole), and p-nitrobenzoic acid (74 g, 0.44 mole) in 800 ml of dry tetrahydrofuran is cooled to 0° C. Into this clear solution, diethyl azodicarboxylate (70 ml, 0.44 mole) is dropped slowly and the resulting mixture is stirred for 1 hour at 0° C. The reaction mixture, while keeping the temperature at 0° C., is diluted with 500 ml of dry methanol and a solution of sodium methoxide (26 g, 0.481 mole) in methanol (300 ml) is dropped into this. The contents are stirred at 0° C. for 2 hours. The solvent is evaporated and the residue is dissolved in 800 ml of dry acetonitrile followed by the addition of potassium carbonate (153 g, 1.1 mole) md 1,2,4-triazole (76 g, 1.11 mole). The resulting mixture is refluxed for 4 hour under nitrogen. After cooling, the solid is removed by suction filtration and washed with ethylacetate (2×1 L). The fine solid from the filtrate is removed over a bed of celite. The filtrate is concentrated under reduced pressure and the residue is dissolved in 800 ml of ethylacetate. The resulting solution is washed with water (2×100 ml), brine and the organic phase is dried over sodium sulfate. The contents are suction filtered. The filtrate is cooled and a steady stream of anhydrous HCl gas is passed until this solution is saturated. The title compound 9d, as hydrochloride, is isolated by suction filtration.

$^1$H-NMR (DMSO-$d_6$) δ: 0.81(d, 3H, J=6.29, —$CH_3$), 4.20(m, 1H, —CH), 4.67–4.85(ABq, 2H, —$CH_2$), 6.83–6.93(m, 1H, Ar—H), 7.09–7.31(m, 2H, Ar—H), 7.99 (s, 1H, Het-H), 8.81 (s, 1 H, Het-H) ppm.

REFERENCES

1. Heeres, J., Backx, L. J. J. and Cutsem, J. V. *J. Med. Chem.*, 1984, 27, 894–900.
2. European Patent #0 612 734 A1.
3. Tasaka, A., Tamura, N., Matsushita, Y., Teranishi, K., Hayashi, R., Okonogi, K. and Itoh, K. *Chem. Pharm. Bull.*, 1993, 41(6), 1035–1042.
4. U.S. patent application Ser. No. US 08/786,376.
5. Konosu, T., Miyaoka, T., Tazima, Y., Oida, S. *Chem. Pharm. Bull.*, 39(9) 2241–2246 (1991).
6. Klunder, J. M., Ko, S. Y. and Sharpless, K. B. *J. Org. Chem.* 1986, 51, 3710–3712.
7. (a) Mitsunobu, O. and Yamada, M. *Bull. Chem. Soc., Jpn.*, 40, 1967, 2380.
   (b) Mitsunobu, O. and Eguchi, M. *Bull. Chem. Soc., Jpn.*, 44, 1971, 3427.
8. Girijavallabhan, V. M., Gangulay, A. K., Pinto, P. A. and Sarre, O Z. Bioorganic & Medicinal Chemistry Letters 1(7), 1991, 349.

We claim:

1. A compound of formula 5

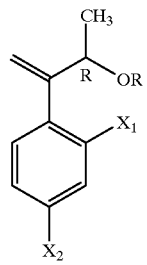

wherein $X_1$ and $X_2$ are each independently selected from the group consisting of hydrogen, chlorine, bromine, fluorine, $C_1$–$C_6$ alkyl group and $C_1$–$C_6$ alkoxy group, wherein the $C_1$–$C_6$ alkyl and $C_1$–$C_6$ alkoxy groups are unsubstituted or have a substituent selected from the group consisting of chlorine, bromine and fluorine; and R is a protecting group.

2. A method of producing a compound of formula 5b,

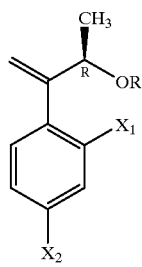

comprising reacting a compound of formula 4b

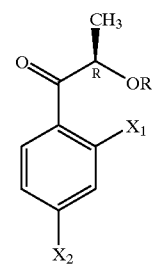

wherein $X_1$ and $X_2$ are each independently selected from the group consisting of hydrogen, chlorine, bromine, fluorine, $C_1$–$C_6$ alkyl group and $C_1$–$C_6$ alkoxy group, wherein the $C_1$–$C_6$ alkyl and $C_1$–$C_6$ alkoxy groups are unsubstituted or have a substituent selected from the group consisting of chlorine, bromine and fluorine; and R is a protecting group, with methyl triphenyl phosphonium bromide to produce the compound of formula 5b.

3. The method of claim 2, wherein the reacting step is conducted in the presence of a bis(trimethylsilyl)amide salt.

4. A method of producing a compound of formula 5a,

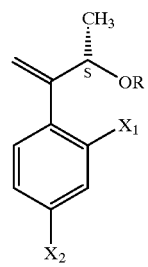

comprising reacting a compound of formula 4a

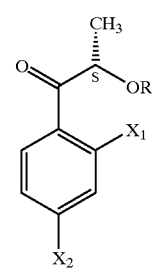

wherein $X_1$ and $X_2$ are each independently selected from the group consisting of hydrogen, chlorine, bromine, fluorine, $C_1$–$C_6$ alkyl group and $C_1$–$C_6$ alkoxy group, wherein the $C_1$–$C_6$ alkyl and $C_1$–$C_6$ alkoxy groups are unsubstituted or have a substituent selected from the group consisting of chlorine, bromine and fluorine; and R is a protecting group, with methyl triphenyl phosphonium bromide to produce the compound of formula 5a.

5. The method of claim 4, wherein the reacting step is conducted in the presence of a bis(trimethylsilyl)amide salt.

6. A method of producing a compound of formula 6a,

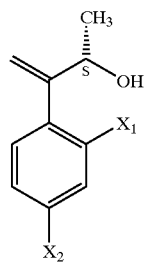
6a wherein $X_1$ and $X_2$ are each independently selected from the group consisting of hydrogen, chlorine, bromine, fluorine, $C_1$–$C_6$ alkyl group and $C_1$–$C_6$ alkoxy group, wherein the $C_1$–$C_6$ alkyl and $C_1$–$C_6$ alkoxy groups are unsubstituted or have a substituent selected from the group consisting of chlorine, bromine and fluorine, comprising reacting a compound of formula 5a

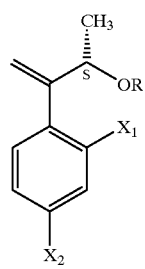
5a wherein $X_1$ and $X_2$ are as defined above; and R is a protecting group, with pyridinium p-toluene sulfonate to produce the compound of formula 6a.

7. A method of producing a compound of formula 6b,

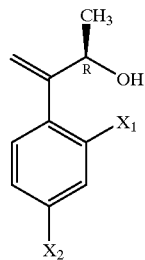
6b wherein $X_1$ and $X_2$ are each independently selected from the group consisting of hydrogen, chlorine, bromine, fluorine, $C_1$–$C_6$ alkyl group and $C_1$–$C_6$ alkoxy group, wherein the $C_1$–$C_6$ alkyl and $C_1$–$C_6$ alkoxy groups are unsubstituted or have a substituent selected from the group consisting of chlorine, bromine and fluorine, comprising reacting a compound of formula 5b

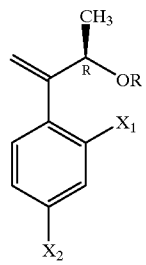
5b wherein $X_1$ and $X_2$ are as defined above; and R is a protecting group, with pyridinium p-toluene sulfonate to produce the compound of formula 6b.

8. A method of producing a compound of formula 7a,

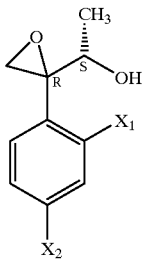
7a wherein $X_1$ and $X_2$ are each independently selected from the group consisting of hydrogen, chlorine, bromine, fluorine, $C_1$–$C_6$ alkyl group and $C_1$–$C_6$ alkoxy group, wherein the $C_1$–$C_6$ alkyl and $C_1$–$C_6$ alkoxy groups are unsubstituted or have a substituent selected from the group consisting of chlorine, bromine and fluorine, comprising reacting a compound of formula 6a

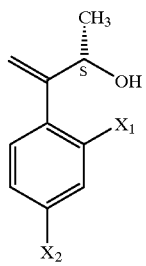
6a wherein $X_1$ and $X_2$ are as defined above, with tert-butyl hydroperoxide in the presence of titanium isopropoxide and a chiral tartrate to produce the compound of formula 7a.

9. A method of producing a compound of formula 7c,

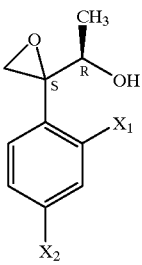
7c wherein $X_1$ and $X_2$ are each independently selected from the group consisting of hydrogen, chlorine, bromine, fluorine, $C_1$–$C_6$ alkyl group and $C_1$–$C_6$ alkoxy group, wherein the $C_1$–$C_6$ alkyl and $C_1$–$C_6$ alkoxy groups are unsubstituted or have a substituent selected from the group consisting of chlorine, bromine and fluorine, comprising reacting a compound of formula 6b

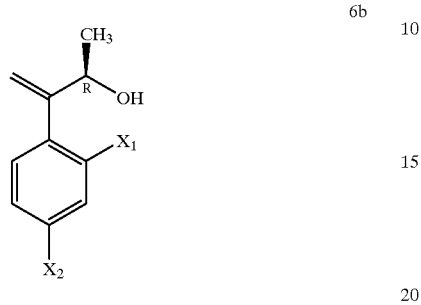

6b wherein $X_1$ and $X_2$ are as defined above, with tert-butyl hydroperoxide in the presence of titanium isopropoxide and a chiral tartrate to produce the compound of formula 7c.

10. A method of producing a compound of formula 7b,

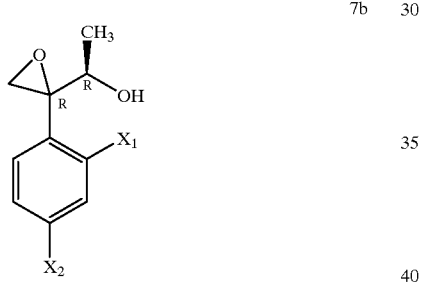

7b wherein $X_1$ and $X_2$ are each independently selected from the group consisting of hydrogen, chlorine, bromine, fluorine, $C_1$–$C_6$ alkyl group and $C_1$–$C_6$ alkoxy group, wherein the $C_1$–$C_6$ alkyl and $C_1$–$C_6$ alkoxy groups are unsubstituted or have a substituent selected from the group consisting of chlorine, bromine and fluorine, comprising reacting, a compound of formula 8a

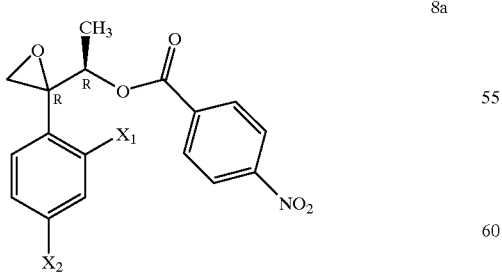

8a wherein $X_1$ and $X_2$ are as defined above, with a methoxide salt to produce the compound of formula 7b.

11. A method of producing a compound of formula 7d,

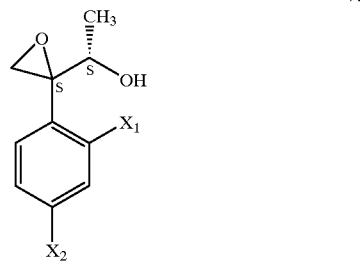

7d wherein $X_1$ and $X_2$ are each independently selected from the group consisting of hydrogen, chlorine, bromine, fluorine, $C_1$–$C_6$ alkyl group and $C_1$–$C_6$ alkoxy group, wherein the $C_1$–$C_6$ alkyl and $C_1$–$C_6$ alkoxy groups are unsubstituted or have a substituent selected from the group consisting of chlorine, bromine and fluorine, comprising reacting a compound of formula 8c

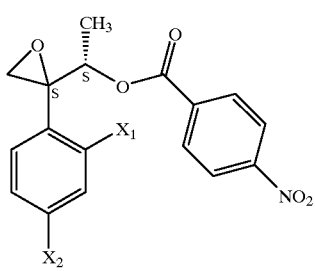

8c wherein $X_1$ and $X_2$ are as defined above, with a methoxide salt to produce the compound of formula 7d.

12. A compound of formula 8a,

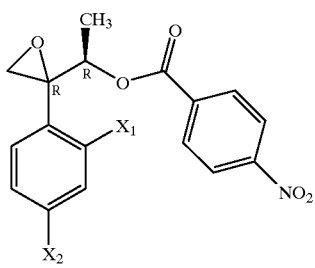

8a wherein $X_1$ and $X_2$ are each independently selected from the group consisting of hydrogen, chlorine, bromine, fluorine, $C_1$–$C_6$ alkyl group and $C_1$–$C_6$ alkoxy group, wherein the $C_1$–$C_6$ alkyl and $C_1$–$C_6$ alkoxy groups are unsubstituted or have a substituent selected from the group consisting of chlorine, bromine and fluorine.

13. A method of producing a compound of formula 8a,

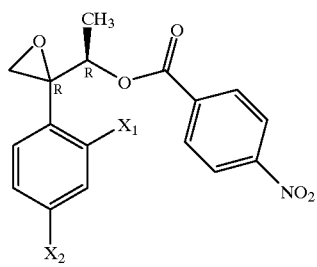

8a wherein $X_1$ and $X_2$ are each independently selected from the group consisting of hydrogen, chlorine, bromine, fluorine, $C_1$–$C_6$ alkyl group and $C_1$–$C_6$ alkoxy group, wherein the $C_1$–$C_6$ alkyl and $C_1$–$C_6$ alkoxy groups are unsubstituted or have a substituent selected from the group consisting of chlorine, bromine and fluorine, comprising reacting a compound of formula 7a

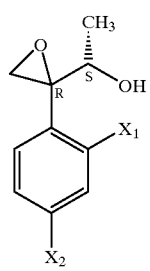

7a wherein $X_1$ and $X_2$ are as defined above, with p-nitrobenzoic acid to produce the compound of formula 8a.

14. The method of claim 13, wherein the reacting step is conducted in the presence of triphenyl phosphine and diethyl azodicarboxylate.

15. A compound of formula 8c,

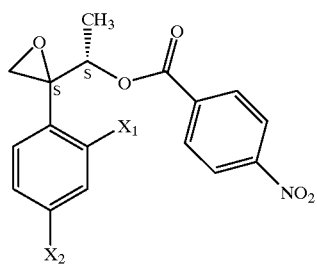

8c wherein $X_1$ and $X_2$ are each independently selected from the group consisting of hydrogen, chlorine, bromine, fluorine, $C_1$–$C_6$ alkyl group and $C_1$–$C_6$ alkoxy group, wherein the $C_1$–$C_6$ alkyl and $C_1$–$C_6$ alkoxy groups are unsubstituted or have a substituent selected from the group consisting of chlorine, bromine and fluorine.

16. A method of producing a compound of formula 8c,

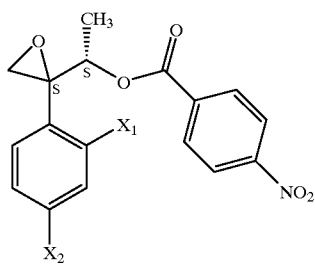

8c wherein $X_1$ and $X_2$ are each independently selected from the group consisting of hydrogen, chlorine, bromine, fluorine, $C_1$–$C_6$ alkyl group and $C_1$–$C_6$ alkoxy group, wherein the $C_1$–$C_6$ alkyl and $C_1$–$C_6$ alkoxy groups are unsubstituted or have a substituent selected from the group consisting of chlorine, bromine and fluorine, comprising reacting a compound of formula 7c

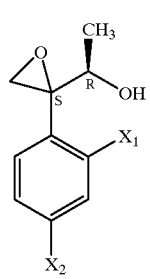

7c wherein $X_1$ and $X_2$ are as defined above, with p-nitrobenzoic acid to produce the compound of formula 8c.

17. The method of claim 16, wherein the reacting step is conducted in the presence of triphenyl phosphine and diethyl azodicarboxylate.

18. A method of producing a compound of formula 7a,

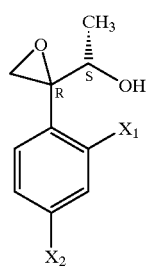

7a wherein $X_1$ and $X_2$ are each independently selected from the group consisting of hydrogen, chlorine, bromine, fluorine, $C_1$–$C_6$ alkyl group and $C_1$–$C_6$ alkoxy group, wherein the $C_1$–$C_6$ alkyl and $C_1$–$C_6$ alkoxy groups are unsubstituted or have a substituent selected from the group consisting of chlorine, bromine and fluorine, the method comprising (a) reacting a compound of formula 4a

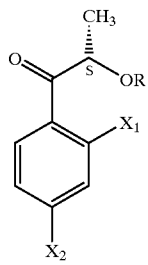
4a wherein $X_1$ and $X_2$ are as defined above; and R is a protecting group, with methyl triphenyl phosphonium bromide to produce a compound of formula 5a,

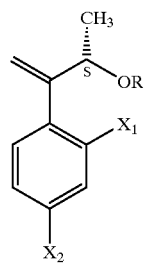
5a wherein $X_1$, $X_2$ and R are as defined above;

(b) thereafter reacting the compound of formula 5a with pyridinium p-toluene sulfonate to produce a compound of formula 6a,

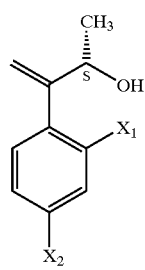
6a wherein $X_1$ and $X_2$ are as defined above; and (c) thereafter reacting the compound of formula 6a with tert-butyl hydroperoxide in the presence of titanium isopropoxide and a chiral tartrate to produce the compound of formula 7a.

19. The method of claim 18, wherein steps (a)–(c) are conducted in sequence without intervening purification steps.

20. A method of producing a compound of formula 7c.

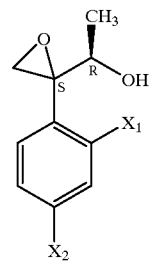
7c wherein $X_1$ and $X_2$ are each independently selected from the group consisting of hydrogen, chlorine, bromine, fluorine, $C_1$–$C_6$ alkyl group and $C_1$–$C_6$ alkoxy group, wherein the $C_1$–$C_6$ alkyl and $C_1$–$C_6$ alkoxy groups are unsubstituted or have a substituent selected from the group consisting of chlorine, bromine and fluorine, the method comprising (a) reacting a compound of formula 4b

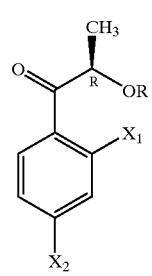
4b wherein $X_1$ and $X_2$ are as defined above; and R is a protecting group, with methyl triphenyl phosphonium bromide to produce a compound of formula 5b,

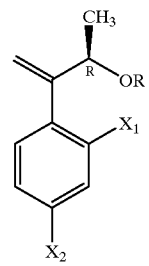
5b wherein $X_1$, $X_2$ and R are as defined above;

(b) thereafter reacting the compound of formula 5b with pyridinium p-toluene sulfonate to produce a compound of formula 6b,

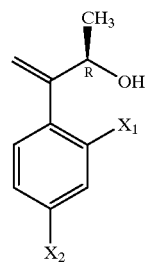

6b wherein $X_1$ and $X_2$ are as defined above; and (c) thereafter reacting the compound of formula 6b with tert-butyl hydroperoxide in the presence of titanium isopropoxide and a chiral tartrate to produce the compound of formula 7c.

21. The method of claim 20, wherein steps (a)–(c) are conducted in sequence without intervening purification steps.

22. A method of producing a compound of formula 9b,

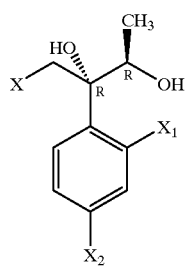

9b wherein $X_1$ and $X_2$ are each independently selected from the group consisting of hydrogen, chlorine, bromine, fluorine, $C_1$–$C_6$ alkyl group and $C_1$–$C_6$ alkoxy group, wherein the $C_1$–$C_6$ alkyl and $C_1$–$C_6$ alkoxy groups are unsubstituted or have a substituent selected from the group consisting of chlorine, bromine and fluorine; and X is selected from the group consisting of (1) $N(R_1)(R_2)$, wherein $R_1$ and $R_2$ are each independently hydrogen or phenyl, wherein the phenyl is unsubstituted or substituted with chlorine, bromine, fluorine, $NO_2$, $C_1$–$C_6$ alkyl group and $C_1$–$C_6$ alkoxy group, wherein the $C_1$–$C_6$ alkyl and $C_1$–$C_6$ alkoxy groups are unsubstituted or have a substituent selected from the group consisting of chlorine, bromine, fluorine and phenyl, wherein the phenyl is unsubstituted or substituted with chlorine, bromine, fluorine, $NO_2$, $C_1$–$C_6$ alkyl group and $C_1$–$C_6$ alkoxy group;

(2) S—$R_1$, therein $R_1$ is as defined above;

(3) O—$R_1$, wherein $R_1$ is as defined above;

(4) S(O)—$R_1$, wherein $R_1$ is as defined above;

(5) $S(O_2)$—$R_1$, wherein $R_1$ is as defined above; and (6) a five, six or seven membered heterocycle with 1–3 heteroatoms each independently selected from the group consisting of N, S, S(O), $S(O_2)$ and O, wherein the heterocycle is attached to the remainder of the compound via a heteroatom or a carbon, the method comprising (a) reacting a compound of formula 7a

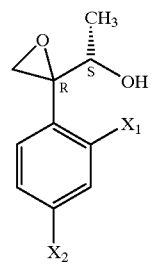

7a wherein $X_1$ and $X_2$ are as defined above, with p-nitrobenzoic acid to produce a compound of formula 8a,

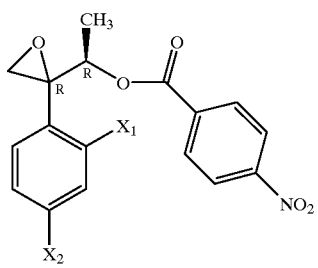

8a wherein $X_1$ and $X_2$ are as defined above;

(b) thereafter reacting the compound of formula 8a with a methoxide salt to produce a compound of formula 7b,

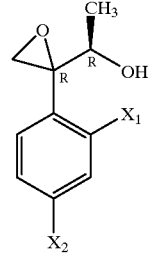

7b wherein $X_1$ and $X_2$ are as defined above; and (c) thereafter reacting the compound of formula 7b with a salt of X, wherein X is as defined above, to produce the compound of formula 9b.

23. The method of claim 22, wherein steps (a)–(c) are conducted in sequence without intervening purification steps.

24. A method of producing a compound of formula 9d,

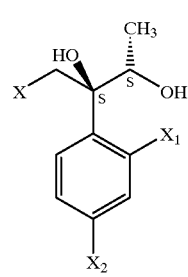

9d wherein $X_1$ and $X_2$ are each independently selected from the group consisting of hydrogen, chlorine, bromine, fluorine, $C_1$–$C_6$ alkyl group and $C_1$–$C_6$ alkoxy group, wherein the $C_1$–$C_6$ alkyl and $C_1$–$C_6$ alkoxy groups are unsubstituted or have a substituent selected from the group consisting of chlorine, bromine and fluorine; and X is selected from the group consisting of (1) $N(R_1)(R_2)$, wherein $R_1$ and $R_2$ are each independently hydrogen or phenyl, wherein the phenyl is unsubstituted or substituted with chlorine, bromine, fluorine, $NO_2$, $C_1$–$C_6$ alkyl group and $C_1$–$C_6$ alkoxy group, wherein the $C_1$–$C_6$ alkyl and $C_1$–$C_6$ alkoxy groups are unsubstituted or have a substituent selected from the group consisting of chlorine, bromine, fluorine and phenyl, wherein the phenyl is unsubstituted or substituted with chlorine, bromine, fluorine, $NO_2$, $C_1$–$C_6$ alkyl group and $C_1$–$C_6$ alkoxy group;

(2) S—$R_1$, wherein $R_1$ is as defined above;

(3) O—$R_1$, wherein $R_1$ is as defined above;

(4) S(O)—$R_1$, wherein $R_1$ is as defined above;

(5) $S(O_2)$—$R_1$, wherein $R_1$ is as defined above; and (6) a five, six or seven membered heterocycle with 1–3 heteroatoms each independently selected from the group consisting of N, S, S(O), $S(O_2)$ and O, wherein the heterocycle i<; attached to the remainder of the compound via a heteroatom or a carbon, the method comprising (a) reacting a compound of formula 7c

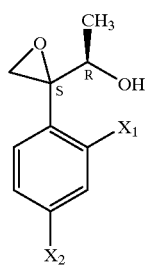

7c wherein $X_1$ and $X_2$ are as defined above, with p-nitrobenzoic acid to produce a compound of formula 8c,

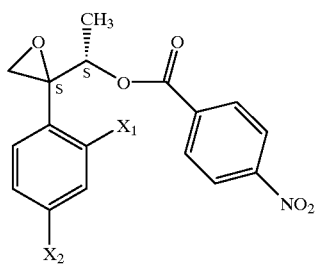

8c wherein $X_1$ and $X_2$ are as defined above;

(b) thereafter reacting the compound of formula 8c with a methoxide salt to produce a compound of formula 7d,

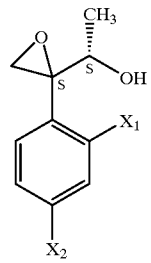

7d wherein $X_1$ and $X_2$ are as defined above; and (c) thereafter reacting the compound of formula 7d with a salt of X, wherein X is as defined above, to produce the compound of formula 9d.

25. The method of claim 24, wherein steps (a)–(c) are conducted in sequence without intervening purification steps.

26. A method of producing a compound of formula 9a,

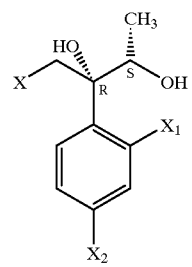

9a wherein $X_1$ and $X_2$ are each independently selected from the group consisting of hydrogen, chlorine, bromine, fluorine, $C_1$–$C_6$ alkyl group and $C_1$–$C_6$ alkoxy group, wherein the $C_1$–$C_6$ alkyl and $C_1$–$C_6$ alkoxy groups are unsubstituted or have a substituent selected from the group consisting of chlorine, bromine and fluorine; and X is selected from the group consisting of (1) $N(R_1)(R_2)$, wherein $R_1$ and $R_2$ are each independently hydrogen or phenyl, wherein the phenyl is unsubstituted or substituted with chlorine, bromine, fluorine, $NO_2$, $C_1$–$C_6$ alkyl group and $C_1$–$C_6$ alkoxy group, wherein the $C_1$–$C_6$ alkyl and $C_1$–$C_6$ alkoxy groups are unsubstituted or have a substituent selected from the group consisting of chlorine, bromine, fluorine and phenyl, wherein the phenyl is unsubstituted or substituted with chlorine, bromine, fluorine, $NO_2$, $C_1$–$C_6$ alkyl group and $C_1$–$C_6$ alkoxy group;

(2) S—$R_1$, wherein $R_1$ is as defined above;

(3) O—$R_1$, wherein $R_1$ is as defined above;

(4) S(O)—$R_1$, wherein $R_1$ is as defined above;

(5) $S(O_2)$—$R_1$, wherein $R_1$ is as defined above; and (6) a five, six or seven membered heterocycle with 1–3 heteroatoms each independently selected from the group consisting of N, S, S(O), $S(O_2)$ and O, wherein the heterocycle is attached to the remainder of the compound via a heteroatom or a carbon, the method comprising reacting a compound of formula 7a

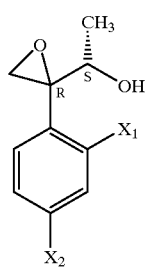

7a wherein $X_1$ and $X_2$ are as defined above, with a salt of X, wherein X is as defined above, to produce the compound of formula 9a.

27. A method of producing a compound of formula 9c,

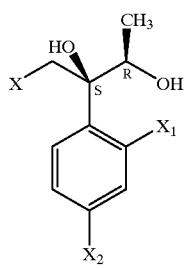

9c wherein $X_1$ and $X_2$ are each independently selected from the group consisting of hydrogen, chlorine., bromine, fluorine, $C_1$–$C_6$ alkyl group and $C_1$–$C_6$ alkoxy group, wherein the $C_1$–$C_6$ alkyl and $C_1$–$C_6$ alkoxy groups are unsubstituted or have a substituent selected from the group consisting of chlorine, bromine and fluorine; and X is selected from the group consisting of (1) $N(R_1)(R_2)$, wherein $R_1$ and $R_2$ are each independently hydrogen or phenyl, wherein the phenyl is unsubstituted or substituted with chlorine, bromine, fluorine, $NO_2$, $C_1$–$C_6$ alkyl group and $C_1$–$C_6$ alkoxy group, wherein the $C_1$–$C_6$ alkyl and $C_1$–$C_6$ alkoxy groups are unsubstituted or have a substituent selected from the group consisting of chlorine, bromine, fluorine and phenyl, wherein the phenyl is unsubstituted or substituted with chlorine, bromine, fluorine, $NO_2$, $C_1$–$C_6$ alkyl group and $C_1$–$C_6$ alkoxy group;

(2) S—$R_1$, wherein $R_1$ is as defined above;

(3) O—$R_1$, wherein $R_1$ is as defined above;

(4) S(O)—$R_1$, wherein $R_1$ is as defined above;

(5) $S(O_2)$—$R_1$, wherein $R_1$ is as defined above; and (6) a five, six or seven membered heterocycle with 1–3 heteroatoms each independently selected from the group consisting of N, S, S(O), $S(O_2)$ and O, wherein the heterocycle is attached to the remainder of the compound via a heteroatom or a carbon, the method comprising reacting a compound of formula 7c

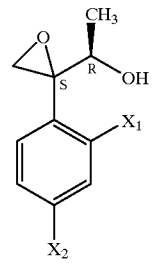

7c wherein $X_1$ and $X_2$ are as defined above, with a salt of X, wherein X is as defined above, to produce the compound of formula 9c.

28. A method of producing a compound of formula 9b,

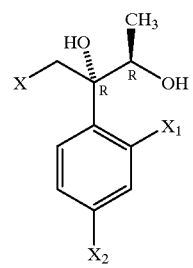

9b wherein $X_1$ and $X_2$ are each independently selected from the group consisting of hydrogen, chlorine, bromine, fluorine, $C_1$–$C_6$ alkyl group and $C_1$–$C_6$ alkoxy group, wherein the $C_1$–$C_6$ alkyl and $C_1$–$C_6$ alkoxy groups are unsubstituted or have a substituent selected from the group consisting of chlorine, bromine and fluorine; and X is selected from the group consisting of (1) $N(R_1)(R_2)$, wherein $R_1$ and $R_2$ are each independently hydrogen or phenyl, wherein the phenyl is unsubstituted or substituted with chlorine, bromine, fluorine, $NO_2$, $C_1$–$C_6$ alkyl group and $C_1$–$C_6$ alkoxy group, wherein the $C_1$–$C_6$ alkyl and $C_1$–$C_6$ alkoxy groups are unsubstituted or have a substituent selected from the group consisting of chlorine, bromine, fluorine and phenyl, wherein the phenyl is unsubstituted or substituted with chlorine, bromine, fluorine, $NO_2$, $C_1$–$C_6$ alkyl group and $C_1$–$C_6$ alkoxy group;

(2) S—$R_1$, wherein $R_1$ is as defined above;

(3) O—$R_1$, wherein $R_1$ is as defined above;

(4) S(O)—$R_1$, wherein $R_1$ is as defined above;

(5) $S(O_2)$—$R_1$, wherein $R_1$ is as defined above; and (6) a five, six or seven membered heterocycle with 1–3 heteroatoms each independently selected from the group consisting of N, S, S(O), $S(O_2)$ and O, wherein the heterocycle is attached to the remainder of the compound via a heteroatom or a carbon, the method comprising reacting a compound of formula 7b,

47

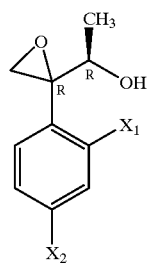
7b wherein $X_1$ and $X_2$ are as defined above, with a salt of X, wherein X is as defined above, to produce the compound of formula 9b.

29. A method of producing a compound of formula 9d,

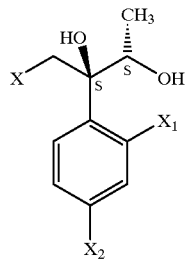
9d wherein $X_1$ and $X_2$ are each independently selected from the group consisting of hydrogen, chlorine, bromine, fluorine, $C_1$–$C_6$ alkyl group and $C_1$–$C_6$ alkoxy group, wherein the $C_1$–$C_6$ alkyl and $C_1$–$C_6$ alkoxy groups are unsubstituted or have a substituent selected from the group consisting of chlorine, bromine and fluorine; and X is selected from the group consisting of (1) $N(R_1)(R_2)$, wherein $R_1$ and $R_2$ are each independently hydrogen or phenyl, wherein the phenyl is unsubstituted or substituted with chlorine, bromine, fluorine, $NO_2$, $C_1$–$C_6$ alkyl group and $C_1$–$C_6$ alkoxy group, wherein the $C_1$–$C_6$ alkyl and $C_1$–$C_6$ alkoxy groups are unsubstituted or have a substituent selected from the group consisting of chlorine, bromine, fluorine and phenyl, wherein the phenyl is unsubstituted or substituted with chlorine, bromine, fluorine, $NO_2$, $C_1$–$C_6$ alkyl group and $C_1$–$C_6$ alkoxy group;

(2) S—$R_1$, wherein $R_1$ is as defined above;

(3) O—$R_1$, wherein $R_1$ is as defined above;

(4) S(O)—$R_1$, wherein $R_1$ is as defined above;

(5) S($O_2$)—$R_1$, wherein $R_1$ is as defined above; and (6) a five, six or seven membered heterocycle with 1–3 heteroatoms each independently selected from the group consisting of N, S, S(O), S($O_2$) and O, wherein the heterocycle is attached to the remainder of the compound via a heteroatom or a carbon, the method comprising reacting a compound of formula 7d,

48

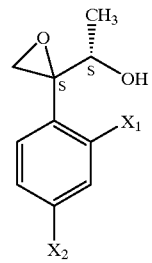
7d wherein $X_1$ and $X_2$ are as defined above, with a salt of X, wherein X is as defined above, to produce the compound of formula 9d.

30. A method of producing a compound of formula 7c,

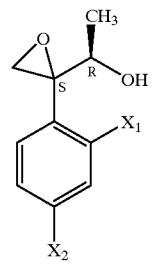
7c wherein $X_1$ and $X_2$ are each independently selected from the group consisting of hydrogen, chlorine, bromine, fluorine, $C_1$–$C_6$ alkyl group and $C_1$–$C_6$ alkoxy group, wherein the $C_1$–$C_6$ alkyl and $C_1$–$C_6$ alkoxy groups are unsubstituted or have a substituent selected from the group consisting of chlorine, bromine and fluorine, comprising reacting a compound of formula 5b

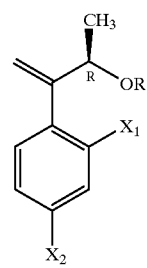
5b wherein $X_1$ and $X_2$ are as defined above; and R is a protecting group,
with pyridinium p-toluene sulfonate to produce a compound of formula 6b

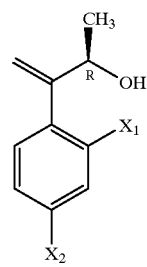
6b wherein $X_1$ and $X_2$ are as defined above, and reacting the compound of formula 6b with tert-butyl hydroperoxide in the presence of titanium isopropoxide and a chiral tartrate to produce the compound of formula 7c.

31. A method of producing a compound of formula 9c,

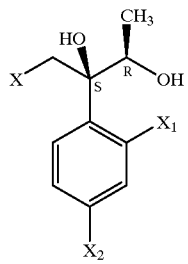

9c wherein $X_1$ and $X_2$ are each independently selected from the group consisting of hydrogen, chlorine, bromine, fluorine, $C_1$–$C_6$ alkyl group and $C_1$–$C_6$ alkoxy group, wherein the $C_1$–$C_6$ alkyl and $C_1$–$C_6$ alkoxy groups are unsubstituted or have a substituent selected from the group consisting of chlorine, bromine and fluorine; and X is selected from the group consisting of (1) $N(R_1)(R_2)$, wherein $R_1$ and $R_2$ are each independently hydrogen or phenyl, wherein the phenyl is unsubstituted or substituted with chlorine, bromine, fluorine, $NO_2$, $C_1$–$C_6$ alkyl group and $C_1$–$C_6$ alkoxy group, wherein the $C_1$–$C_6$ alkyl and $C_1$–$C_6$ alkoxy groups are unsubstituted or have a substituent selected from the group consisting of chlorine, bromine, fluorine and phenyl, wherein the phenyl is unsubstituted or substituted with chlorine, bromine, fluorine, $NO_2$, $C_1$–$C_6$ alkyl group and $C_1$–$C_6$ alkoxy group;

(2) S—$R_1$, wherein $R_1$ is as defined above;

(3) O—$R_1$, wherein $R_1$ is as defined above;

(4) S(O)—$R_1$, wherein $R_1$ is as defined above;

(5) $S(O_2)$—$R_1$, wherein $R_1$ is as defined above; and (6) a five, six or seven membered heterocycle with 1–3 heteroatoms each independently selected from the group consisting of N, S, S(O), $S(O_2)$ and O, wherein the heterocycle is attached to the remainder of the compound via a heteroatom or a carbon, the method comprising reacting a compound of formula 5b

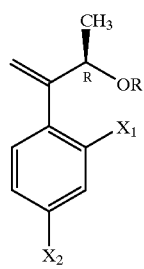

5b wherein $X_1$ and $X_2$ are as defined above; and R is a protecting group, with pyridinium p-toluene sulfonate to produce a compound of formula 6b

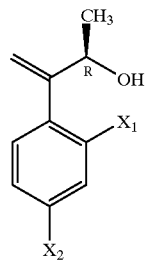

6b wherein $X_1$ and $X_2$ are as defined above, and reacting the compound of formula 6b with tert-butyl hydroperoxide in the presence of titanium isopropoxide and a chiral tartrate to produce a compound of formula 7c

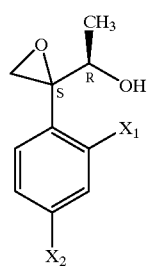

7c wherein $X_1$ and $X_2$ are as defined above, and reacting the compound of formula 7c with a salt of X, wherein X is as defined above, to produce the compound of formula 9c.

32. A method of producing a compound of formula 9d,

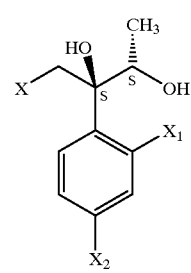

9d wherein $X_1$ and $X_2$ are each independently selected from the group consisting of hydrogen, chlorine, bromine, fluorine, $C_1$–$C_6$ alkyl group and $C_1$–$C_6$ alkoxy group, wherein the $C_1$–$C_6$ alkyl and $C_1$–$C_6$ alkoxy groups are unsubstituted or have a substituent selected from the group consisting of chlorine, bromine and fluorine; and X is selected from the group consisting of (1) $N(R_1)(R_2)$, wherein $R_1$ and $R_2$ are each independently hydrogen or phenyl, wherein the phenyl is unsubstituted or substituted with chlorine, bromine, fluorine, $NO_2$, $C_1$–$C_6$ alkyl group and $C_1$–$C_6$ alkoxy group, wherein the $C_1$–$C_6$ alkyl and $C_1$–$C_6$ alkoxy groups are unsubstituted or have a substituent selected from the group consisting of chlorine, bromine, fluorine and phenyl, wherein the phenyl is unsubstituted or substituted with chlorine, bromine, fluorine, $NO_2$, $C_1$–$C_6$ alkyl group and $C_1$–$C_6$ alkoxy group;

(2) S—$R_1$, wherein $R_1$ is as defined above;
(3) O—$R_1$, wherein $R_1$ is as defined above;
(4) S(O)—$R_1$, wherein $R_1$ is as defined above;
(5) S($O_2$)—$R_1$, wherein $R_1$ is as defined above; and
(6) a five, six or seven membered heterocycle with 1–3 heteroatoms each independently selected from the group consisting of N, S, S(O), S($O_2$) and O, wherein the heterocycle is attached to the remainder of the compound via a heteroatom or a carbon, the method comprising reacting a compound of formula 8c

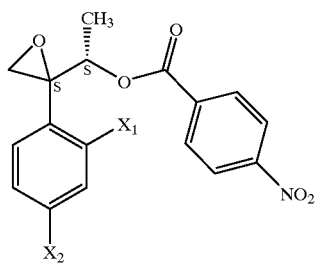

8c wherein $X_1$ and $X_2$ are as defined above, with a methoxide salt to produce a compound of formula 7d

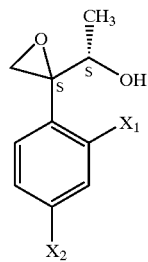

7d wherein $X_1$ and $X_2$ are as defined above, and reacting the compound of formula 7d with a salt of X, wherein X is as defined above, to produce the compound of formula 9d.

33. A method of producing a compound of formula 9b,

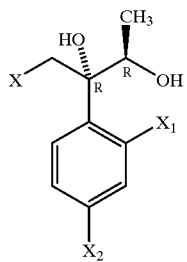

9b wherein $X_1$ and $X_2$ are each independently selected from the group consisting of hydrogen, chlorine, bromine, fluorine, $C_1$–$C_6$ alkyl group and $C_1$–$C_6$ alkoxy group, wherein the $C_1$–$C_6$ alkyl and $C_1$–$C_6$ alkoxy groups are unsubstituted or have a substituent selected from the group consisting of chlorine, bromine and fluorine; and X is selected from the group consisting of
(1) N($R_1$)($R_2$), wherein $R_1$ and $R_2$ are each independently hydrogen or phenyl, wherein the phenyl is unsubstituted or substituted with chlorine, bromine, fluorine, $NO_2$, $C_1$–$C_6$ alkyl group and $C_1$–$C_6$ alkoxy group, wherein the $C_1$–$C_6$ alkyl and $C_1$–$C_6$ alkoxy groups are unsubstituted or have a substituent selected from the group consisting of chlorine, bromine, fluorine and phenyl, wherein the phenyl is unsubstituted or substituted with chlorine, bromine, fluorine, $NO_2$, $C_1$–$C_6$ alkyl group and $C_1$–$C_6$ alkoxy group;
(2) S—$R_1$, wherein $R_1$ is as defined above;
(3) O—$R_1$, wherein $R_1$ is as defined above;
(4) S(O)—$R_1$, wherein $R_1$ is as defined above;
(5) S($O_2$)—$R_1$, wherein $R_1$ is as defined above; and
(6) a five, six or seven membered heterocycle with 1–3 heteroatoms each independently selected from the group consisting of N, S, S(O), S($O_2$) and O, wherein the heterocycle is attached to the remainder of the compound via a heteroatom or a carbon, the method comprising reacting a compound of formula 8a

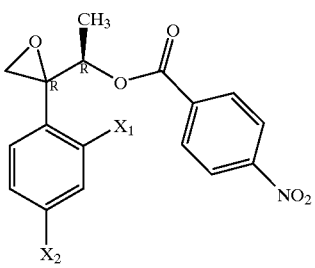

8a wherein $X_1$ and $X_2$ are as defined above, with a methoxide salt to produce a compound of formula 7b

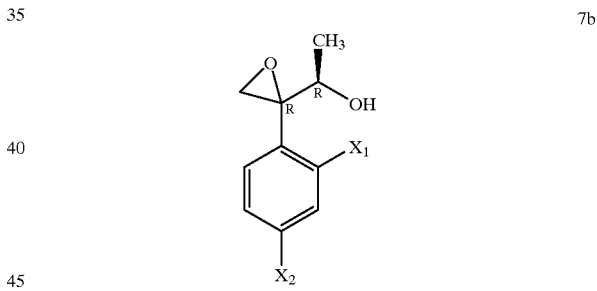

7b wherein $X_1$ and $X_2$ are as defined above, and reacting the compound of formula 7b, with a salt of X, wherein X is as defined above, to produce the compound of formula 9b.

34. A method of producing a compound of formula 8a,

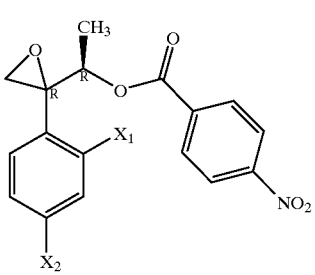

8a wherein $X_1$ and $X_2$ are each independently selected from the group consisting of hydrogen, chlorine, bromine, fluorine, $C_1$–$C_6$ alkyl group and $C_1$–$C_6$ alkoxy group, wherein the $C_1$–$C_6$ alkyl and $C_1$–$C_6$ alkoxy groups are unsubstituted or have a substituent selected from the group consisting of chlorine, bromine and fluorine, comprising reacting a compound of formula 4a

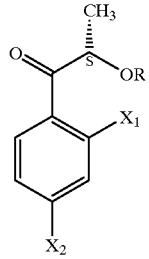

4a wherein $X_1$ and $X_2$ are as defined above; and R is a protecting group,
with methyl triphenyl phosphonium bromide to produce a compound of formula 5a

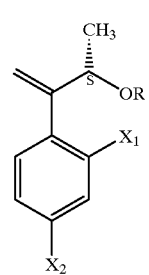

5a wherein $X_1$, $X_2$ and R are as defined above, reacting the compound of formula 5a with pyridinium p-toluene sulfonate to produce a compound of formula 6a

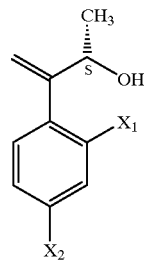

6a wherein $X_1$ and $X_2$ are as defined above, reacting a compound of formula 6a with tert-butyl hydroperoxide in the presence of titanium isopropoxide and a chiral tartrate to produce a compound of formula 7a

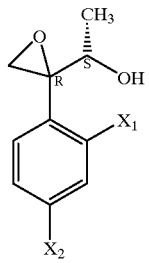

7a wherein $X_1$ and $X_2$ are as defined above, and reacting the compound of formula 7a with p-nitrobenzoic acid to produce the compound of formula 8a.

* * * * *